(12) United States Patent
Chao et al.

(10) Patent No.: US 10,624,790 B2
(45) Date of Patent: Apr. 21, 2020

(54) ELECTRONIC EYEWEAR THERAPY

(71) Applicant: IpVenture, Inc., Los Altos, CA (US)

(72) Inventors: David Chao, Saratoga, CA (US); Zhiyang Guo, Hercules, CA (US); Jason Sweis, San Jose, CA (US); Vivian Liane Rice, Campbell, CA (US); Grace C Sheen, Portland, OR (US); Eric S Hussey, Spokane, WA (US)

(73) Assignee: IpVenture, Inc., San Jose, CA (US)

( * ) Notice: Subject to any disclaimer, the term of this patent is extended or adjusted under 35 U.S.C. 154(b) by 59 days.

(21) Appl. No.: 14/703,875

(22) Filed: May 4, 2015

(65) Prior Publication Data
US 2015/0230988 A1     Aug. 20, 2015

Related U.S. Application Data

(63) Continuation-in-part of application No. 14/217,174, filed on Mar. 17, 2014, now abandoned, which is a
(Continued)

(51) Int. Cl.
*A61F 9/04* (2006.01)
*G02C 7/16* (2006.01)
(Continued)

(52) U.S. Cl.
CPC ............ *A61F 9/045* (2013.01); *A61H 5/005* (2013.01); *G02C 5/2227* (2013.01); *G02C 7/101* (2013.01);
(Continued)

(58) Field of Classification Search
CPC .......... A61F 9/045; G02B 27/22; G02C 7/16; G02C 7/101; G02C 11/10; G02F 1/1313; G02F 1/13306; A61H 5/00; A61H 5/005
(Continued)

(56) References Cited

U.S. PATENT DOCUMENTS 320,558 A   6/1885   Hull
669,949 A   3/1901   Underwood
(Continued)

FOREIGN PATENT DOCUMENTS

CA   2 487 391    12/2003
CN   88203065    11/1988
(Continued)

OTHER PUBLICATIONS

Notice of Allowance for U.S. Appl. No. 14/072,784, dated Jan. 14, 2016.
(Continued)

*Primary Examiner* — Darryl J Collins

(57) ABSTRACT

Embodiments for systems, methods and apparatuses of eyewear are disclosed. One method includes treating a patient with shutter glasses therapy for a relatively short period of time, such as at least a 6 week period; wherein the shutter glasses therapy includes blanking a first lens of shutter glasses being worn by the patient for a first blocking time, blanking a second lens of the shutter glasses being worn by the patient for a second blocking time, and controllably setting at least one of the first blocking time and the second blocking time.

21 Claims, 18 Drawing Sheets

Combining left and right temple-controlled switch on/off, the application might control:

1、System on/off

2、Display functioning cycle-time

3、Battery life

4、Adjust LCD frequency

5、Reset

Related U.S. Application Data continuation-in-part of application No. 13/615,447, filed on Sep. 13, 2012, now abandoned.

(60) Provisional application No. 61/988,186, filed on May 3, 2014, provisional application No. 61/792,481, filed on Mar. 15, 2013, provisional application No. 61/556,083, filed on Nov. 4, 2011, provisional application No. 61/535,341, filed on Sep. 15, 2011.

(51) Int. Cl.

| | |
|---|---|
| *A61H 5/00* | (2006.01) |
| *G02F 1/13* | (2006.01) |
| *G02F 1/133* | (2006.01) |
| *G02C 5/22* | (2006.01) |
| *G02C 7/10* | (2006.01) |
| *G02C 11/00* | (2006.01) |
| *G06F 19/00* | (2018.01) |

(52) U.S. Cl.
CPC ............. *G02C 7/104* (2013.01); *G02C 7/16* (2013.01); *G02C 11/10* (2013.01); *G02F 1/1313* (2013.01); *G02F 1/13306* (2013.01); *G06F 19/3481* (2013.01); *A61H 2201/165* (2013.01); *A61H 2201/501* (2013.01); *A61H 2201/5015* (2013.01); *A61H 2201/5028* (2013.01); *A61H 2201/5035* (2013.01); *A61H 2201/5038* (2013.01); *A61H 2201/5043* (2013.01); *A61H 2201/5058* (2013.01); *A61H 2201/5066* (2013.01); *A61H 2201/5082* (2013.01); *A61H 2201/5097* (2013.01); *G02C 2200/22* (2013.01); *G02C 2200/26* (2013.01); *G02C 2200/28* (2013.01)

(58) Field of Classification Search
USPC ...................................... 351/158, 203; 606/4
See application file for complete search history.

(56) References Cited

U.S. PATENT DOCUMENTS

| | | |
|---|---|---|
| 1,255,265 A | 2/1918 | Zachara |
| 1,917,745 A | 7/1933 | Weiss |
| 2,249,572 A | 7/1941 | Lieber |
| 2,638,532 A | 5/1953 | Brady |
| 2,794,085 A | 5/1957 | De Angelis |
| 2,818,511 A | 12/1957 | Ullery et al. |
| 2,830,132 A | 4/1958 | Borg |
| 2,874,230 A | 2/1959 | Carlson |
| 2,904,670 A | 9/1959 | Calmes |
| 3,060,308 A | 10/1962 | Fortuna |
| 3,597,054 A | 8/1971 | Winter |
| 3,710,115 A | 1/1973 | Jubb |
| 3,858,001 A | 12/1974 | Bonne |
| 3,883,701 A | 5/1975 | Delorenzo |
| 4,165,487 A | 8/1979 | Corderman |
| 4,254,451 A | 3/1981 | Cochran, Jr. |
| 4,283,127 A | 8/1981 | Rosenwinkel et al. |
| 4,322,585 A | 3/1982 | Liautaud |
| 4,348,664 A | 9/1982 | Boschetti et al. |
| 4,389,217 A | 6/1983 | Baughman et al. |
| 4,526,473 A | 7/1985 | Zahn, III |
| 4,535,244 A | 8/1985 | Burnham |
| 4,608,492 A | 8/1986 | Burnham |
| 4,683,587 A | 7/1987 | Silverman |
| 4,751,691 A | 6/1988 | Perera |
| 4,757,714 A | 7/1988 | Purdy et al. |
| 4,773,095 A | 9/1988 | Zwicker et al. |
| 4,806,011 A | 2/1989 | Bettinger |
| 4,822,160 A | 4/1989 | Tsai |
| 4,822,161 A | 4/1989 | Jimmy |
| 4,851,686 A | 7/1989 | Pearson |
| 4,856,086 A | 8/1989 | McCullough |
| 4,859,047 A | 8/1989 | Badewitz |
| 4,882,769 A | 11/1989 | Gallimore |
| 4,904,078 A | 2/1990 | Gorike |
| 4,942,629 A | 7/1990 | Stadlmann |
| 4,962,469 A | 10/1990 | Ono et al. |
| 4,967,268 A | 10/1990 | Lipton et al. |
| 4,985,632 A | 1/1991 | Bianco et al. |
| 5,008,548 A | 4/1991 | Gat |
| 5,015,086 A | 5/1991 | Okaue et al. |
| 5,020,150 A | 5/1991 | Shannon |
| 5,026,151 A | 6/1991 | Waltuck et al. |
| 5,036,311 A | 7/1991 | Moran et al. |
| 5,050,150 A | 9/1991 | Ikeda |
| 5,064,410 A | 11/1991 | Frenkel et al. |
| 5,093,576 A | 3/1992 | Edmond et al. |
| 5,106,179 A | 4/1992 | Kamaya et al. |
| 5,148,023 A | 9/1992 | Hayashi et al. |
| 5,151,600 A | 9/1992 | Black |
| 5,161,250 A | 11/1992 | Ianna et al. |
| 5,172,256 A | 12/1992 | Sethofer et al. |
| 5,264,877 A | 11/1993 | Hussey |
| 5,306,917 A | 4/1994 | Black et al. |
| 5,353,378 A | 10/1994 | Hoffman et al. |
| 5,359,370 A | 10/1994 | Mugnier |
| 5,359,444 A | 10/1994 | Piosenka et al. |
| 5,367,345 A | 11/1994 | da Silva |
| 5,379,464 A | 1/1995 | Schleger et al. |
| 5,382,986 A | 1/1995 | Black et al. |
| 5,394,005 A | 2/1995 | Brown et al. |
| 5,452,026 A | 9/1995 | Marcy, III |
| 5,452,480 A | 9/1995 | Ryden |
| 5,455,637 A | 10/1995 | Kallman et al. |
| 5,455,640 A | 10/1995 | Gertsikov |
| 5,457,751 A | 10/1995 | Such |
| 5,463,428 A | 10/1995 | Lipton et al. |
| 5,500,532 A | 3/1996 | Kozicki |
| D369,167 S | 4/1996 | Hanson et al. |
| 5,510,961 A | 4/1996 | Peng |
| 5,513,384 A | 4/1996 | Brennan et al. |
| 5,533,130 A | 7/1996 | Staton |
| 5,541,641 A | 7/1996 | Shimada |
| 5,581,090 A | 12/1996 | Goudjil |
| 5,585,871 A * | 12/1996 | Linden ............... A63B 71/0686 351/158 |
| 5,589,398 A | 12/1996 | Krause et al. |
| 5,590,417 A | 12/1996 | Rydbeck |
| 5,606,743 A | 2/1997 | Vogt et al. |
| 5,608,808 A | 3/1997 | da Silva |
| 5,634,201 A | 5/1997 | Mooring |
| 5,671,035 A | 9/1997 | Barnes |
| 5,686,727 A | 11/1997 | Reenstra et al. |
| 5,694,475 A | 12/1997 | Boyden |
| 5,715,323 A | 2/1998 | Walker |
| 5,737,436 A | 4/1998 | Boyden et al. |
| 5,818,381 A | 10/1998 | Williams |
| 5,835,185 A | 11/1998 | Kallman et al. |
| 5,900,720 A | 5/1999 | Kallman et al. |
| 5,903,395 A | 5/1999 | Rallison et al. |
| 5,941,837 A | 8/1999 | Amano et al. |
| 5,946,071 A | 8/1999 | Feldman |
| 5,949,516 A | 9/1999 | McCurdy |
| 5,966,746 A | 10/1999 | Reedy et al. |
| 5,980,037 A | 11/1999 | Conway |
| 5,988,812 A | 11/1999 | Wingate |
| 5,991,085 A | 11/1999 | Rallison et al. |
| 5,992,996 A | 11/1999 | Sawyer |
| 5,995,592 A | 11/1999 | Shirai et al. |
| 6,010,216 A | 1/2000 | Jesiek |
| 6,013,919 A | 1/2000 | Schneider et al. |
| 6,028,627 A | 2/2000 | Helmsderfer |
| 6,046,455 A | 4/2000 | Ribi et al. |
| 6,060,321 A | 5/2000 | Hovorka |
| 6,061,580 A | 5/2000 | Altschul et al. |
| 6,091,546 A | 7/2000 | Spitzer |
| 6,091,832 A | 7/2000 | Shurman et al. |
| 6,115,177 A | 9/2000 | Vossler |
| 6,132,681 A | 10/2000 | Faran et al. |
| 6,145,983 A | 11/2000 | Schiffer |

(56) References Cited

U.S. PATENT DOCUMENTS

| | | | |
|---|---|---|---|
| 6,154,552 A | 11/2000 | Koroljow et al. | |
| 6,176,576 B1 | 1/2001 | Green et al. | |
| 6,225,897 B1 | 5/2001 | Doyle et al. | |
| 6,231,181 B1 | 5/2001 | Swab | |
| 6,236,969 B1 | 5/2001 | Ruppert et al. | |
| 6,243,578 B1 | 6/2001 | Koike | |
| 6,259,367 B1 | 7/2001 | Klein | |
| 6,270,466 B1 | 8/2001 | Weinstein et al. | |
| 6,292,213 B1 | 9/2001 | Jones | |
| 6,292,685 B1 | 9/2001 | Pompei | |
| 6,301,367 B1 | 10/2001 | Boyden et al. | |
| 6,307,526 B1 | 10/2001 | Mann | |
| 6,343,858 B1 | 2/2002 | Zelman | |
| 6,349,001 B1 | 2/2002 | Spitzer | |
| 6,349,422 B1 | 2/2002 | Schleger et al. | |
| 6,409,335 B1 | 6/2002 | Lipawsky | |
| 6,409,338 B1 | 6/2002 | Jewell | |
| 6,426,719 B1 | 7/2002 | Nagareda et al. | |
| 6,431,705 B1 | 8/2002 | Linden | |
| 6,474,816 B2 | 11/2002 | Butler et al. | |
| 6,478,736 B1 | 11/2002 | Mault | |
| 6,506,142 B2 | 1/2003 | Itoh et al. | |
| 6,511,175 B2 | 1/2003 | Hay et al. | |
| 6,513,532 B2 | 2/2003 | Mault et al. | |
| 6,517,203 B1 | 2/2003 | Blum et al. | |
| 6,539,336 B1 | 3/2003 | Vock et al. | |
| 6,542,081 B2 | 4/2003 | Torch | |
| 6,546,101 B1 | 4/2003 | Murray et al. | |
| 6,554,763 B1 | 4/2003 | Amano et al. | |
| 6,582,075 B1 | 6/2003 | Swab et al. | |
| 6,619,799 B1 | 9/2003 | Blum et al. | |
| 6,629,076 B1 | 9/2003 | Haken | |
| 6,729,726 B2 | 5/2004 | Miller et al. | |
| 6,736,759 B1 | 5/2004 | Stubbs et al. | |
| 6,764,194 B1 | 7/2004 | Cooper | |
| 6,769,767 B2 | 8/2004 | Swab et al. | |
| 6,788,309 B1 | 9/2004 | Swan et al. | |
| 6,792,401 B1 | 9/2004 | Nigro et al. | |
| 6,816,314 B2 | 11/2004 | Shimizu et al. | |
| 6,824,265 B1 | 11/2004 | Harper | |
| 6,871,951 B2 | 3/2005 | Blum et al. | |
| 6,879,930 B2 | 4/2005 | Sinclair et al. | |
| 6,912,386 B1 | 6/2005 | Himberg et al. | |
| 6,929,365 B2 | 8/2005 | Swab et al. | |
| 6,932,090 B1 | 8/2005 | Reschke et al. | |
| 6,947,219 B1 | 9/2005 | Ou | |
| 7,004,582 B2 | 2/2006 | Jannard et al. | |
| 7,013,009 B2 | 3/2006 | Warren | |
| 7,030,902 B2 | 4/2006 | Jacobs | |
| 7,031,667 B2 | 4/2006 | Horiguchi | |
| 7,033,025 B2 | 4/2006 | Winterbotham | |
| 7,059,717 B2 | 6/2006 | Bloch | |
| 7,073,905 B2 | 7/2006 | Da Pra' | |
| 7,079,876 B2 | 7/2006 | Levy | |
| 7,123,215 B2 | 10/2006 | Nakada | |
| 7,192,136 B2 | 3/2007 | Howell et al. | |
| 7,255,437 B2 | 8/2007 | Howell et al. | |
| 7,265,358 B2 | 9/2007 | Fontaine | |
| 7,274,292 B2 | 9/2007 | Velhal et al. | |
| 7,289,767 B2 | 10/2007 | Lai | |
| 7,312,699 B2 | 12/2007 | Chornenky | |
| 7,331,666 B2 | 2/2008 | Swab et al. | |
| 7,376,238 B1 | 5/2008 | Rivas et al. | |
| 7,380,936 B2 | 6/2008 | Howell et al. | |
| 7,401,918 B2 | 7/2008 | Howell et al. | |
| 7,405,801 B2 | 7/2008 | Jacobs | |
| 7,429,965 B2 | 9/2008 | Weiner | |
| 7,438,409 B2 | 10/2008 | Jordan | |
| 7,438,410 B1 | 10/2008 | Howell et al. | |
| 7,445,332 B2 | 11/2008 | Jannard et al. | |
| 7,481,531 B2 | 1/2009 | Howell et al. | |
| 7,500,746 B1 | 3/2009 | Howell et al. | |
| 7,500,747 B2 | 3/2009 | Howell et al. | |
| 7,512,414 B2 | 3/2009 | Jannard et al. | |
| 7,527,374 B2 | 5/2009 | Chou | |
| 7,543,934 B2 | 6/2009 | Howell et al. | |
| 7,581,833 B2 | 9/2009 | Howell et al. | |
| 7,621,634 B2 | 11/2009 | Howell et al. | |
| 7,648,236 B1 | 1/2010 | Dobson | |
| 7,677,723 B2 | 3/2010 | Howell et al. | |
| 7,760,898 B2 | 7/2010 | Howell et al. | |
| 7,771,046 B2 | 8/2010 | Howell et al. | |
| 7,792,552 B2 | 9/2010 | Thomas et al. | |
| 7,806,525 B2 | 10/2010 | Howell et al. | |
| 7,922,321 B2 | 4/2011 | Howell et al. | |
| 7,976,159 B2 | 7/2011 | Jacobs et al. | |
| 8,109,629 B2 | 2/2012 | Howell et al. | |
| 8,142,015 B2 | 3/2012 | Paolino | |
| 8,174,569 B2 * | 5/2012 | Tanijiri | G02B 27/0176 348/115 |
| 8,337,013 B2 | 12/2012 | Howell et al. | |
| 8,430,507 B2 | 4/2013 | Howell et al. | |
| 8,434,863 B2 | 5/2013 | Howell et al. | |
| 8,465,151 B2 | 6/2013 | Howell et al. | |
| 8,485,661 B2 | 7/2013 | Yoo et al. | |
| 8,500,271 B2 | 8/2013 | Howell et al. | |
| 8,770,742 B2 | 7/2014 | Howell et al. | |
| 8,905,542 B2 | 12/2014 | Howell et al. | |
| 9,033,493 B2 | 5/2015 | Howell et al. | |
| 9,244,292 B2 | 1/2016 | Swab et al. | |
| 9,400,390 B2 | 7/2016 | Osterhout et al. | |
| 9,405,135 B2 | 8/2016 | Sweis et al. | |
| 9,488,520 B2 | 11/2016 | Howell et al. | |
| 9,547,184 B2 | 1/2017 | Howell et al. | |
| 9,690,121 B2 | 6/2017 | Howell et al. | |
| 10,042,186 B2 | 8/2018 | Chao et al. | |
| 10,060,790 B2 | 8/2018 | Howell et al. | |
| 10,061,144 B2 | 8/2018 | Howell et al. | |
| 10,310,296 B2 | 6/2019 | Howell et al. | |
| 10,345,625 B2 | 7/2019 | Howell et al. | |
| 10,359,311 B2 | 7/2019 | Howell et al. | |
| 2001/0005230 A1 | 6/2001 | Ishikawa | |
| 2001/0028309 A1 | 10/2001 | Torch | |
| 2001/0050754 A1 * | 12/2001 | Hay | A61H 5/00 351/213 |
| 2002/0017997 A1 | 2/2002 | Felkowitz | |
| 2002/0021407 A1 | 2/2002 | Elliott | |
| 2002/0081982 A1 | 6/2002 | Schwartz et al. | |
| 2002/0084990 A1 | 7/2002 | Peterson, III | |
| 2002/0089639 A1 | 7/2002 | Starner et al. | |
| 2002/0090103 A1 | 7/2002 | Calisto, Jr. | |
| 2002/0098877 A1 | 7/2002 | Glezerman | |
| 2002/0101568 A1 | 8/2002 | Eberl et al. | |
| 2002/0109600 A1 | 8/2002 | Mault et al. | |
| 2002/0140899 A1 | 10/2002 | Blum et al. | |
| 2002/0159023 A1 | 10/2002 | Swab | |
| 2002/0197961 A1 | 12/2002 | Warren | |
| 2003/0018274 A1 | 1/2003 | Takahashi et al. | |
| 2003/0022690 A1 | 1/2003 | Beyda et al. | |
| 2003/0032449 A1 | 2/2003 | Giobbi | |
| 2003/0062046 A1 | 4/2003 | Wiesmann et al. | |
| 2003/0065257 A1 | 4/2003 | Mault et al. | |
| 2003/0067585 A1 | 4/2003 | Miller et al. | |
| 2003/0068057 A1 | 4/2003 | Miller et al. | |
| 2003/0083591 A1 | 5/2003 | Edwards et al. | |
| 2003/0214630 A1 | 11/2003 | Winterbotham | |
| 2003/0226978 A1 | 12/2003 | Ribi et al. | |
| 2004/0000733 A1 | 1/2004 | Swab et al. | |
| 2004/0029582 A1 | 2/2004 | Swab et al. | |
| 2004/0059212 A1 | 3/2004 | Abreu | |
| 2004/0063378 A1 | 4/2004 | Nelson | |
| 2004/0096078 A1 | 5/2004 | Lin | |
| 2004/0100384 A1 | 5/2004 | Chen et al. | |
| 2004/0128737 A1 | 7/2004 | Gesten | |
| 2004/0150986 A1 | 8/2004 | Chang | |
| 2004/0156012 A1 | 8/2004 | Jannard et al. | |
| 2004/0157649 A1 | 8/2004 | Jannard et al. | |
| 2004/0160571 A1 | 8/2004 | Jannard | |
| 2004/0160572 A1 | 8/2004 | Jannard | |
| 2004/0160573 A1 | 8/2004 | Jannard et al. | |
| 2004/0197002 A1 | 10/2004 | Atsumi et al. | |
| 2004/0227219 A1 | 11/2004 | Su | |
| 2005/0067580 A1 | 3/2005 | Fontaine | |
| 2005/0078274 A1 | 4/2005 | Howell et al. | |

(56) References Cited

U.S. PATENT DOCUMENTS

| | | |
|---|---|---|
| 2005/0088365 A1 | 4/2005 | Yamazaki et al. |
| 2005/0201585 A1 | 9/2005 | Jannard et al. |
| 2005/0213026 A1 | 9/2005 | Da Pra' |
| 2005/0230596 A1 | 10/2005 | Howell et al. |
| 2005/0238194 A1 | 10/2005 | Chornenky |
| 2005/0239502 A1 | 10/2005 | Swab et al. |
| 2005/0248717 A1 | 11/2005 | Howell et al. |
| 2005/0248718 A1 | 11/2005 | Howell et al. |
| 2005/0248719 A1 | 11/2005 | Howell et al. |
| 2005/0264752 A1 | 12/2005 | Howell et al. |
| 2006/0001827 A1 | 1/2006 | Howell et al. |
| 2006/0003803 A1 | 1/2006 | Thomas et al. |
| 2006/0023158 A1 | 2/2006 | Howell et al. |
| 2006/0034478 A1 | 2/2006 | Davenport |
| 2006/0107822 A1 | 5/2006 | Bowen |
| 2006/0132382 A1 | 6/2006 | Jannard |
| 2007/0030442 A1 | 2/2007 | Howell et al. |
| 2007/0035830 A1 | 2/2007 | Matveev et al. |
| 2007/0046887 A1 | 3/2007 | Howell et al. |
| 2007/0055888 A1 | 3/2007 | Miller et al. |
| 2007/0098192 A1 | 5/2007 | Sipkema |
| 2007/0109491 A1 | 5/2007 | Howell et al. |
| 2007/0186330 A1 | 8/2007 | Howell et al. |
| 2007/0200927 A1 | 8/2007 | Krenik |
| 2007/0208531 A1 | 9/2007 | Darley et al. |
| 2007/0270663 A1 | 11/2007 | Ng et al. |
| 2007/0271065 A1 | 11/2007 | Gupta et al. |
| 2007/0271116 A1 | 11/2007 | Wysocki et al. |
| 2007/0271387 A1 | 11/2007 | Lydon et al. |
| 2007/0279584 A1 | 12/2007 | Howell et al. |
| 2008/0062338 A1* | 3/2008 | Herzog .................. G02C 7/101 349/13 |
| 2008/0068559 A1 | 3/2008 | Howell et al. |
| 2008/0144854 A1 | 6/2008 | Abreu |
| 2008/0151175 A1* | 6/2008 | Gross .................... G02C 7/086 351/45 |
| 2008/0151179 A1 | 6/2008 | Howell et al. |
| 2008/0158506 A1 | 7/2008 | Fuziak |
| 2008/0218684 A1 | 9/2008 | Howell et al. |
| 2008/0262392 A1 | 10/2008 | Ananny et al. |
| 2008/0278678 A1 | 11/2008 | Howell et al. |
| 2009/0059159 A1 | 3/2009 | Howell et al. |
| 2009/0059381 A1 | 3/2009 | Jannard |
| 2009/0073375 A1 | 3/2009 | Nakada |
| 2009/0141233 A1 | 6/2009 | Howell et al. |
| 2009/0147215 A1 | 6/2009 | Howell et al. |
| 2009/0156128 A1 | 6/2009 | Franson et al. |
| 2009/0251660 A1* | 10/2009 | Figler .................. G02F 1/13452 351/158 |
| 2009/0251661 A1 | 10/2009 | Fuziak, Jr. |
| 2009/0296044 A1 | 12/2009 | Howell et al. |
| 2010/0061579 A1 | 3/2010 | Rickards et al. |
| 2010/0079356 A1 | 4/2010 | Hoellwarth |
| 2010/0110368 A1 | 5/2010 | Chaum |
| 2010/0245754 A1 | 9/2010 | Matsumoto et al. |
| 2010/0296045 A1 | 11/2010 | Agnoli et al. |
| 2010/0309426 A1 | 12/2010 | Howell et al. |
| 2011/0102734 A1 | 5/2011 | Howell et al. |
| 2011/0164122 A1 | 7/2011 | Hardacker |
| 2011/0187990 A1 | 8/2011 | Howell et al. |
| 2011/0241796 A1 | 10/2011 | Boger et al. |
| 2011/0273365 A1 | 11/2011 | West et al. |
| 2012/0033061 A1 | 2/2012 | Ko et al. |
| 2012/0050668 A1 | 3/2012 | Howell et al. |
| 2012/0133885 A1 | 3/2012 | Howell et al. |
| 2012/0176580 A1* | 7/2012 | Sonsino .................. G02C 7/14 351/158 |
| 2013/0072828 A1 | 3/2013 | Sweis et al. |
| 2013/0077175 A1 | 3/2013 | Hotta et al. |
| 2013/0201440 A1 | 8/2013 | Howell et al. |
| 2013/0308089 A1 | 11/2013 | Howell et al. |
| 2014/0132913 A1 | 5/2014 | Sweis et al. |
| 2014/0176902 A1 | 6/2014 | Sweis et al. |
| 2014/0198293 A1 | 7/2014 | Sweis et al. |
| 2014/0268008 A1 | 9/2014 | Howell et al. |
| 2014/0268013 A1 | 9/2014 | Howell et al. |
| 2014/0268017 A1 | 9/2014 | Sweis et al. |
| 2014/0361185 A1 | 12/2014 | Howell et al. |
| 2015/0085245 A1 | 3/2015 | Howell et al. |
| 2015/0253590 A1 | 9/2015 | Howell et al. |
| 2016/0246075 A9 | 8/2016 | Howell et al. |
| 2016/0302992 A1 | 10/2016 | Sweis et al. |
| 2017/0068117 A9 | 3/2017 | Howell et al. |
| 2017/0074721 A1 | 3/2017 | Howell et al. |
| 2017/0090219 A1 | 3/2017 | Howell et al. |
| 2017/0131575 A1 | 5/2017 | Howell et al. |
| 2017/0146829 A1 | 5/2017 | Howell et al. |
| 2018/0314079 A1 | 11/2018 | Chao et al. |
| 2018/0335650 A1 | 11/2018 | Howell et al. |
| 2018/0348050 A1 | 12/2018 | Howell et al. |
| 2019/0033623 A1 | 1/2019 | Howell et al. |
| 2019/0187492 A1 | 6/2019 | Howell et al. |
| 2019/0278110 A1 | 9/2019 | Howell et al. |
| 2019/0285913 A1 | 9/2019 | Howell et al. |
| 2019/0310132 A1 | 10/2019 | Howell et al. |
| 2019/0318589 A1 | 10/2019 | Howell et al. |

FOREIGN PATENT DOCUMENTS

| | | |
|---|---|---|
| CN | 89214222.7 | 3/1990 |
| CN | 90208199.3 | 11/1990 |
| DE | 10123226 A1 | 11/2002 |
| EP | 1134491 A2 | 9/2001 |
| FR | 2530039 A1 | 1/1984 |
| GB | 1467982 | 3/1977 |
| JP | 58-113912 | 7/1983 |
| JP | 58-113914 | 7/1983 |
| JP | 02-181722 | 7/1990 |
| JP | 09-017204 | 1/1997 |
| JP | 10-161072 | 6/1998 |
| JP | 2000-039595 | 2/2000 |
| JP | 2002 341059 A | 11/2002 |
| JP | 2005-151292 | 6/2005 |
| TW | 484711 | 6/2001 |
| WO | WO 1997/12205 A1 | 4/1997 |
| WO | WO 99/50706 A1 | 10/1999 |
| WO | WO 2001/06298 A1 | 1/2001 |
| WO | WO 2002/06881 A2 | 1/2002 |
| WO | WO 2003/069394 A1 | 8/2003 |
| WO | 2003/100503 A2 | 12/2003 |
| WO | WO 2003/100368 A1 | 12/2003 |
| WO | WO 2004/012477 A2 | 2/2004 |
| WO | WO 2004/025554 A1 | 3/2004 |
| WO | WO 10/0141514 A2 | 12/2010 |

OTHER PUBLICATIONS

Notice of Allowance for U.S. Appl. No. 14/072,784, dated Apr. 7, 2016.
Office Action for U.S. Appl. No. 15/193,155, dated Jun. 8, 2017.
Office Action for U.S. Appl. No. 14/190,352, dated May 4, 2017.
Office Action for U.S. Appl. No. 14/072,784, dated Jul. 27, 2015.
Office Action for U.S. Appl. No. 14/072,784, dated Oct. 29, 2015.
Office Action for U.S. Appl. No. 15/193,155, dated Sep. 26, 2016.
Office Action for U.S. Appl. No. 14/490,352, dated Oct. 26, 2016.
Office Action for U.S. Appl. No. 13/615,447, dated Jan. 26, 2017.
"±1.5g Dual Axis Micromachined Accelerometer", Freescale Semiconductor, Inc., Motorola Semiconductor Technical Data, MMA6260Q, Jun. 2004, pp. 1-7.
"APA Announces Shipment of the SunUV™ Personal UV Monitor", Press Release, Nov. 7, 2003, pp. 1-3.
"Camera Specs Take Candid Snaps," BBC News, Sep. 18, 2003, pp. 1-3.
"Cardo Wireless Attaching Clips and Wearing Headset," Cardo Systems, Inc., http://www.cardowireless.com/clips.php, downloaded Nov. 27, 2004, pp. 1-3.
"Environmental Health Criteria 14: Ultraviolet Radiation", International Programme on Chemical Safety, World Health Organization Geneva, 1979 http://www.ichem.org., pp. 1-102.
"Exclusive Media Event Marks Debut of Oakley Thump: World's First Digital Audio Eyewear", Oakley Investor Relations, Press Release, Nov. 15, 2004, pp. 1-2.

(56) References Cited

OTHER PUBLICATIONS

"Eyetop", Product-Features, eyetop eyewear, eyetop belt worn, http://www.eyetop.net/products/eyetop/features.asp., downloaded Nov. 6, 2003, pp. 1-2.
"Heart Rate Monitors", http://www.healthgoods.com, downloaded Dec. 4, 2004.
"How is the UV Index Calculated", SunWise Program, U.S. Environmental Protection Agency, http://www.epa.gov/sunwise/uvcalc.html, downloaded Oct. 14, 2004, pp. 1-2.
"Industrial UV Measurements", APA Optics, Inc., http://www.apaoptics.com/uv/, downloaded Jul. 12, 2004, p. 1.
"Motorola and Oakley Introduce First Bluetooth Sunglasses-Cutting Edge RAZRWire Line Offers Consumers On-The-Go Connections", Motorola Mediacenter-Press Release, Feb. 14, 2005, pp. 1-2.
"Oakley Thump: Sunglasses Meet MP3 Player", with image, http://news.designtechnica.com/article4665.html, Jul. 13, 2004.
"Personal UV monitor," Optics.org, http://optics.org/articles/news/6/6/7/1 (downloaded Dec. 20, 2003), Jun. 9, 2000, pp. 1-2.
"SafeSun Personal Ultraviolet Light Meter", http://healthchecksystems.com/safesun.htm, downloaded Jul. 12, 2004, pp. 1-4.
"SafeSun Personal UV Meter", Introduction, Optix Tech Inc., http://www.safesun.com, downloaded Feb. 5, 2004, pp. 1-2.
SafeSun Personal UV Meter, features, Optix Tech Inc., http://www.safesun.com/features.html, downloaded May 1, 2004, pp. 1-2.
"Sharper Image—The FM Pedometer", e-Corporate Gifts.com, http://www.e-corporategifts.com/sr353.html, downloaded Jan. 22, 2005, pp. 1-2.
"Sun UV™ Personal UV Monitor", APA Optics, Inc., http://www.apaoptics.com/sunuv/uvfacts.html, downloaded Dec. 20, 2003, pp. 1-3.
"Ultraviolet Light and Sunglasses", Oberon's Frequently Asked Questions, http://www.oberoncompany.com/OBEnglish/FAQUV.html, downloaded Feb. 5, 2004, pp. 1-2.
"Ultraviolet Light Sensor", Barrett & Associates Engineering, http://www.barrettengineering.com/project_uvs.htm, downloaded Feb. 5, 2004, pp. 1-3.
"Ultraviolet Radiation (UVR)", Forum North, Ontario Ministry of Labour, http://www3.mb.sympatico.ca/~ericc/ULTRAVIOLET%20RADIATION.htm, downloaded Feb. 5, 2004, pp. 1-6.
"What Are Gripples?", Gripping Eyewear, Inc., http://www.grippingeyewear.com/whatare.html, downloaded Nov. 2, 2005.
"With Racing Heart", Skaloud et al., GPS World, Oct. 1, 2001, http://www.gpsworld.com/gpsworld/content/printContentPopup.jsp?id=1805, pp. 1-5.
Abrisa Product Information: Cold Mirrors, Abrisa, Jun. 2001, p. 1.
Abrisa Product Information: Commercial Hot Mirror, Abrisa, Jun. 2001, p. 1.
Alps Spectacle, Air Conduction Glass, Bone Conduction Glass, http://www.alps-inter.com/spec.htm, downloaded Dec. 10, 2003, pp. 1-2.
Altimeter and Compass Watches, http://store.yahoo.com/snowshack/altimeter-watches.html, downloaded May 3, 2004, pp. 1-2.
Pediatric Eye Disease Group,"Randomized Trial of Treatment of Amblyopia in Children Aged 7 to 17 Years," Roy W. Beck, M.D., Ph.D. Section Ed., Originally Published and Reprinted from Arch Ophthalmol, v. 123, Apr. 2005, pp. 437-447, http;//archopht.jamanetwork.com/ by a new England College of Optometry User on Dec. 20, 2012.
Bone Conduction Headgear HG16 Series, "Voiceducer," http://www.temco-j.co.jp/html/English/HG16.html, downloaded Dec. 10, 2003, pp. 1-3.
Carnoy, David, "The Ultimate MP3 Player for Athletes? Could be.", CNET Reviews, May 14, 2004, pp. 1-4.
Clifford, Michelle A., "Accelerometers Jump into the Consumer Goods Market", Sensors Online, http://www.sensorsmag.com, Aug. 2004.
Comfees.com, Adjustable Sports Band Style No. 1243, http://shop.store.yahoo.com/comfees/adsportbansty.html, downloaded Apr. 18, 2003, pp. 1-2.

Cool Last Minute Gift Ideas! UltimateFatBurner Reviews and Articles, http://www.ultimatefatburner.com/gift-ideas.html, downloaded May 10, 2005, pp. 1-3.
Dickie et al. "Eye Contact Sensing Glasses for Attention-Sensitive Wearable Video Blogging," Human Media Lab, Queen's University, Kingston, ON K7L 3N6, Canada, est. Apr. 2004, pp. 1-2.
Dixen, Brian, "Ear-catching", Supertesten, Mobil, Apr. 2003 (estimated), pp. 37-41.
Global Solar UV Index, A Practical Guide, World Health Organization, 2002, pp. 1-28.
Grobart, Sam, "Digit-Sizing Your Computer Data", News Article, Sep., 2004, p. 1.
Holmes, JM et al. "A randomized trial of prescribed patching regimens for treatment of severe amblyopia in children." Ophthalmology, v. 110, Iss.11, Nov. 2003, pp. 2075-2087.
Life Monitor V1.1, Rhusoft Technologies Inc., http://www.rhusoft.com/lifemonitor/, Mar. 1, 2003, pp. 1-6.
Manes, Stephen, "Xtreme Cam", Forbes Magazine, Sep. 5, 2005, p. 96.
Mio, PhysiCal, http://www.gophysical.com/, downloaded Jan. 27, 2004, 5 pages.
Monitoring Athletes Performance—2002 Winter Olympic News from KSL, Jan. 23, 2002, http://2002.ksl.com/news-3885i, pp. 1-3.
Niwa, "UV Index Information", http://www.niwa.cri.nz/services/uvozone/uvi-info, downloaded Jul. 15, 2004, pp. 1-2.
NuVision 60GX Steroscopic Wireless Glasses, Product Information, NuVision by MacNaughton, c. 1997, MacNaughton, Inc., pp. 1-2.
Pärkkä, Juha, et al., "A Wireless Wellness Monitor for Personal Weight Management", VTT Information Technology, Tampere, Finland, Nov. 2000, p. 1.
Pedometer, Model HJ-112, Omron Instruction Manual, Omron Healthcare, Inc., 2003, pp. 1-27.
PNY Announces Executive Attaché USB 2.0 Flash Drive and Pen Series, Press Release, PNY Technologies, Las Vegas, Jan. 8, 2004, pp. 1-2.
PNY Technologies, "Executive Attaché" http://www.pny.com/products/flash/execattache.asp downloaded Nov. 16, 2005.
Polar WM41 and 42 weight management monitor, http://www.simplysports/polar/weight_management/wm41-42.htm, downloaded Jan. 28, 2004, pp. 1-3.
Questions Answers, Pedometer.com, http://www.pedometer.com, downloaded May 5, 2005.
RazrWire, copyright Motorola, Inc., Jul. 2005, 1 page.
Repka MX et al. "A randomized trial of patching regimens for treatment of moderate amblyopia in children." *Arch Ophthalmology* v. 121, No. 5, May 2003, pp. 603-611.
SafeSun Personal UV Meter, Scientific Data, Optix Tech Inc., http://www.safesun.com/scientific.html, downloaded May 1, 2004, pp. 1-3.
SafeSun Sensor, User's Manual, Optix Tech Inc., Jun. 1998, 2 pages.
SafeSun, Personal UV Meter, "Technical Specifications," Optix Tech Inc., http://www.safesun.com/technical.html, downloaded Jul. 12, 2004, pp. 1-2.
SafeSun, Personal UV Meter, Experiments, Optix Tech Inc., http://www.safesun.com/experiments.html, downloaded Feb. 5, 2004, pp. 1-2.
Shades of Fun, Blinking Light Glasses, http://www.shadesoffun.com/Nov/Novpgs-14.html, downloaded Jul. 9, 2005, pp. 1-4.
SportLine Fitness Pedometer—Model 360, UltimateFatBurner Superstore, http://www.ultimatefatburner-store.com/ac_004.html, downloaded May 10, 2005, pp. 1-2.
Steele, Bonnie G. et al., "Bodies in motion: Monitoring daily activity and exercise with motion sensors in people with chronic pulmonary disease", VA Research & Development, Journal of Rehabilitation Research & Development, vol. 40, No. 5, Sep./Oct. 2003, Supplement 2, pp. 45-58.
Stevens, Kathy, "Should I Use a Pedometer When I Walk?", Healtheon/WebMD, Apr. 14, 2000.
Sundgot, Jørgen "2nd-gen Motorola Bluetooth headset", InfoSync World, Mar. 1, 2003, http://www.infosync.no/news/2002/n/2841.html, pp. 1-2.

(56) References Cited

OTHER PUBLICATIONS

SunSensors, Segan Industries, Inc. http://www.segan-ind.com/sunsensor.htm, downloaded Feb. 5, 2004, pp. 1-3.
SunUV™, Personal UV Monitor User's Guide, APA Optics, Inc., 2003 pp. 1-52.
SunUV™, Personal UV Monitor, APA Optics, Inc., http://www.apaoptics.com/sunuv/models.html, downloaded Dec. 20, 2003.
Talking Pedometer, Sportline, Inc., Jun. 2001 (Possibly earlier), 1 page.
The unofficial ELSA 3D Revelator page, Dec. 30, 1999, pp. 1-15.
Top Silicon PIN Photodiode, PD93-21C, Technical Data Sheet, Everlight Electronics Co., Ltd., 2004, pp. 1-9.
UV Light Meter, UVA and UVB measurement, UV-340, Instruction Manual, Lutron, Jun. 2003 (estimated), pp. 1-5.
UV-Smart, UVA/B Monitor, Model EC-960-PW, Instruction Manual, Tanita Corporation of America, Inc., downloaded Nov. 16, 2001.
Vitaminder Personal Carb Counter, http://www.auravita.com/products/AURA/ORBU11420.asp. Downloaded Nov. 15, 2005, pp. 1-4.
Wallace DK et al. "A randomized trial to evaluate 2 hours of daily patching for strabismic and anisometropic amblyopia in children." *Ophthalmology* v. 113, No. 6, Jun. 2006, pp. 904-912.
Yamada et al. "Development of an eye-movement analyser possessing functions for wireless transmission and autocalibration," Med. Biol. Eng. Comput., No. 28, v.4, Jul. 28, 1990, http://link.springer.com/article/10.1007%2FBF02446149?LI=true, pp. 1-2.

* cited by examiner

Combining left and right temple-controlled switch on/off, the application might control:

1、 System on/off

2、 Display functioning cycle-time

3、 Battery life

4、 Adjust LCD frequency

5、 Reset

Selecting a first period of blanking of a first lens of a corrective lens apparatus
1810
Selecting a second period of blanking of a second lens of the corrective lens apparatus
1820
Selecting a frequency of at least one of the blanking of the first lens and the blanking of the second lens
1830
FIGURE 18

ELECTRONIC EYEWEAR THERAPY

CROSS-REFERENCE TO RELATED APPLICATIONS

This patent application claims priority to U.S. patent application Ser. No. 61/988,186, entitled "Electronic Eyewear Therapy", filed on May 3, 2014, which is hereby incorporated by reference.

This patent application is a continuation-in-part of U.S. patent application Ser. No. 14/217,174, entitled, "Electronic Eyewear", filed Mar. 1, 2014, which is hereby incorporated herein by reference, which in turn claims priority to US Provisional Patent Application No. 61/792,481, entitled "Electronic Eyewear," filed Mar. 15, 2013, which is hereby incorporated herein by reference, which in turn is a continuation-in-part of U.S. patent application Ser. No. 13/615,447, entitled, "Shutter Glasses", filed Sep. 13, 2012, which is hereby incorporated herein by reference, which in turn claims priority to US Provisional Patent Application No. 61/535,341, filed Sep. 15, 2011, which is hereby incorporated herein by reference; and US Provisional Patent Application No. 61/556,083, filed Nov. 4, 2011, which is hereby incorporated herein by reference.

FIELD OF THE DESCRIBED EMBODIMENTS

The described embodiments relate generally to electronic eyewear. More particularly, the described embodiments relate to apparatuses, methods and systems for electronic eyewear therapy.

BACKGROUND OF THE INVENTION

In newborn children, the nerves and brain function that control eye movement and image processing begin to converge during the first 9 months after birth. Sometimes this natural process can go wrong and their eyes can start to cross inward (esotropia) or separate outwards (exotropia). This can prevent the brain from receiving simultaneous overlapping images from each eye to provide a true 3D depth realization. Surgery is sometimes needed to bring the eyes back into reasonable alignment but the brain still may suppress one eye or the other. In other situations, though the eyes are aligned, one eye can become dominant and the other "lazy" (amblyopia). Again the brain needs to learn how to process the images from both eyes simultaneously and equally. The nerves that control the eye muscles and receive the input of each eye need to be trained such as for binocular or stereo vision.

In small children with vision problems, the best results happen if therapy is started before the age of six when the wiring becomes mostly permanent. The older the child gets, the harder it is to correct the defects. So their defective eyesight should be corrected as early as possible. However, there are challenges in working with very young children. For example, they have more difficulty comprehending the need for the therapy; and they may not be able to execute instructions for vision therapy, particularly when the tasks are boring to them. The challenge is further exacerbated when the training session requires performing certain tasks repetitively for a long duration of time.

Instead of performing vision therapy, some parents opt for corrective eye surgery. For example, surgery could bring crossed eye back into near alignment. However, even after the surgery, their brain still prefers to use one eye over another. They need to be trained or to be retrained to see with both eyes.

Such eye defects are not limited to small children. Adults may need vision therapy also. For example, according to one study, two or more percent of the population in the United States do not have stereo vision.

Prior methods of treating amblyopia include patching. Patching is an effective therapy for amblyopia when patients are compliant. However compliance, particularly in older children, could be difficult primarily due to the debilitating effects of decreased vision while wearing a patch, along with social, cosmetic, and comfort issues that could make consistent therapy progressively more difficult with increasing age.

It is desirable to have methods, systems and apparatuses for providing vision therapy to address the eye ailments described above.

SUMMARY OF THE INVENTION

An embodiment includes a method of eye therapy. The method includes treating a patient with shutter glasses therapy for a relatively short period of time, such as at least a 6 week period; wherein the shutter glasses therapy includes blanking a first lens of shutter glasses being worn by the patient for a first blocking time, blanking a second lens of the shutter glasses being worn by the patient for a second blocking time, and controllably setting at least one of the first blocking time and the second blocking time.

An embodiment includes an eye therapy system. The eye therapy system includes shutter glasses and a controller. The controller operative to treat a patient with shutter glasses therapy for a relatively short period of time, such as at least a 6 week period, wherein during the shutter glasses therapy the controller is further operative to blank a first lens of shutter glasses being worn by a patient for a first blocking time, blank a second lens of the shutter glasses being worn by the patient for a second blocking time, and controllably set at least one of the first blocking time and the second blocking time.

Other aspects and advantages of the described embodiments will become apparent from the following detailed description, taken in conjunction with the accompanying drawings, illustrating by way of example the principles of the described embodiments.

BRIEF DESCRIPTION OF THE DRAWINGS

FIG. 18 is a flow chart that includes steps of a method of operating shutter glasses, according to an embodiment.

DETAILED DESCRIPTION OF THE INVENTION

Figure 1:
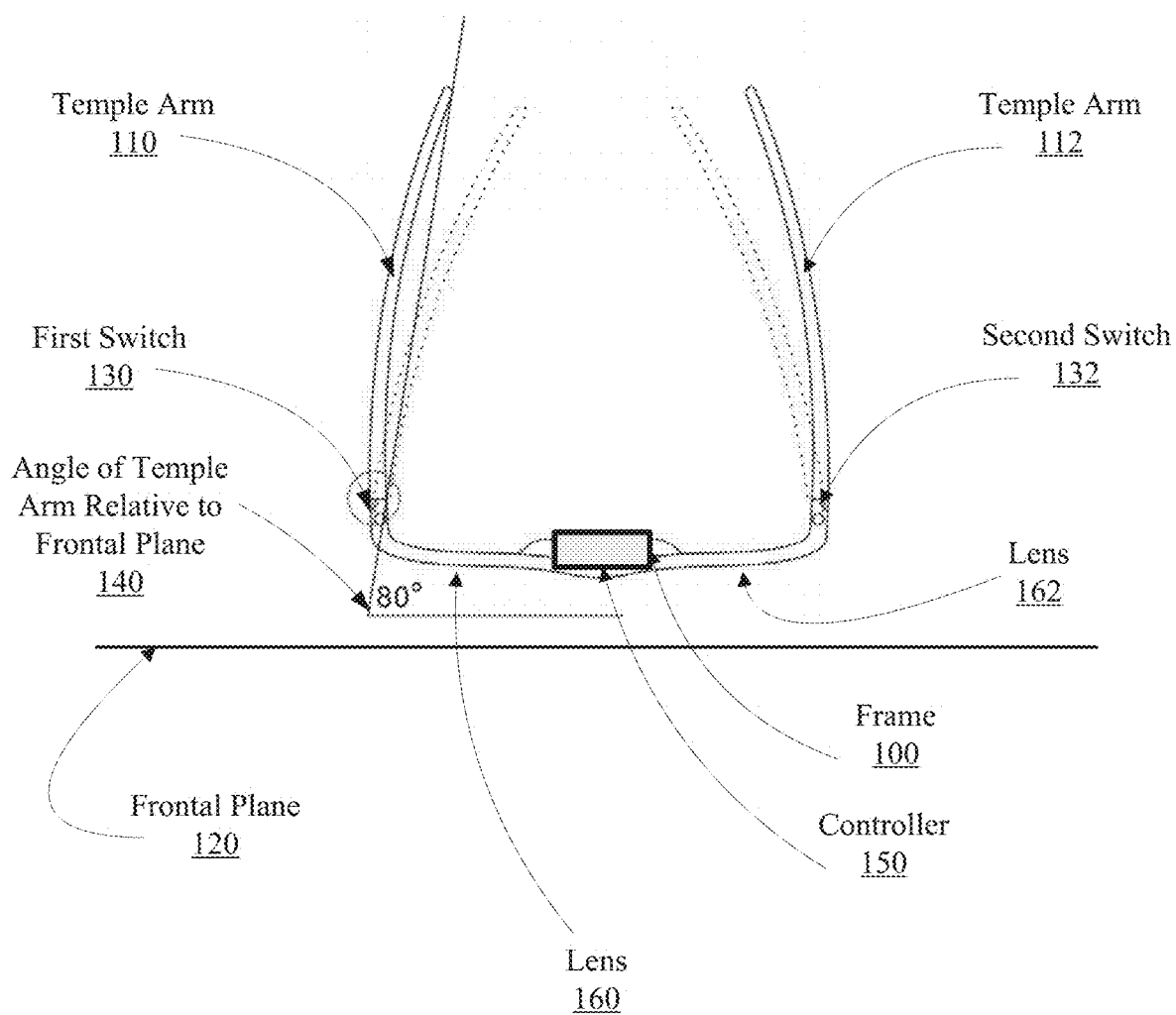
FIG. 1 shows a block diagram of electronic eyewear according to an embodiment.

During the course of therapy utilizing an electronic eyewear of the related applications that have been incorporated by reference into this application (hereinafter "Related Applications"), a patient may become fatigued or tired of wearing the electronic eyewear. Accordingly, at least some of the described embodiments in this application provide for therapy that is substantially optimized to provide desirable results without requiring excessive wearing of the electronic eyewear by the patient. Such embodiments can be particularly useful for younger patients that may not be very tolerant with the therapy.

For an embodiment, the patient does not receive amblyopia treatment 1 month prior to the therapy.

For an embodiment, the patient wears shutter glasses that include LCD lenses that include electronic shuttering, such as glasses disclosed in the Related Applications.

An embodiment includes the application of shutter glasses therapy to the patient. For an embodiment, the therapy includes the patient wearing the shutter glasses approximately 1-2 hours a day, approximately 6-7 days a week, for a relatively short period of time, such as at least approximately 6 weeks. In another embodiment, through experimentation it has been determined that substantial results (improvement in patient condition) are realized by application of the shutter glasses therapy for the relatively short period of time, such as approximately 6 weeks. Additional, but significantly less improvements can be realized for application of the shutter glasses therapy beyond the relatively short period of time, such as 6 weeks.

For an embodiment, the shutter glasses include a shuttering or blanking rate of approximately 7 Hertz, plus or minus approximately 2 Hertz, having a duty cycle of approximately 50%.

For at least some embodiments, during therapy, the patient are able to perform near vision task, such as, reading, homework, computer viewing, and/or video games.

At least one of the described embodiments includes one or more switches located on eyewear for providing commands to a controller of the eyewear, or for monitoring use of the eyewear. For an embodiment, the monitoring can be used by either a patient or a doctor to determine how long (either as a total duration and/or as finite duration of a period of time, such as, a day or a week, or a month) the user has worn the eyewear for therapeutic reason. For an embodiment, the monitoring provides or allows for providing an indicator of how well the user has complied (referred to as compliance) with a therapy recommended by the doctor. For an embodiment, the monitored use and/or compliance is displayable to the user on a display located on the electronic eyewear. For an embodiment, the monitored use and/or compliance is stored for future access (through, for example, an externally connected controller or computer) by the doctor. Base on the monitored use and/or compliance information, the doctor can confirm that the therapy is being properly applied (for example, patient complying to the recommended hours of wear) by the user, or the doctor may determine that the therapy needs to be updated.

For an embodiment, the monitored use and/or compliance is utilized by a user (patient) that has been proscribed the use of one or more of the described embodiments of shutter glasses. For an embodiment, the doctor uses the monitored use and/or compliance information to determine whether the shutter glasses are shuttering (blanking, or first or second blocking times) at the proper frequency and/or time period, or whether the frequency and/or time period of the shuttering should be adjusted. A user can develop a mental fatigue to particular blocking times or frequencies, and new particular blocking times or frequencies can be required to further therapy of the user (patient).

FIG. 1 shows a block diagram of electronic eyewear according to an embodiment. For this embodiment, the electronic eyewear includes a frame 100 that includes a pair of temple arms 110, 112 forming eyewear that is adaptable to hold one or more lenses (for example, lenses 160, 162). The electronic glasses further include at least one switch (for example, a first switch 130 and/or a second switch 132). For an embodiment, the at least one switch is open or closed depending upon an angle of at least one of the temple arms 110, 112 relative to a frontal plane 120 of the one or more lenses.

It is to be understood that while the embodiment of FIG. 1 is described as electronic eyewear, this embodiment includes glasses, goggles and other forms of eyewear, including what are sometimes referred to as "frame-less" glasses. Other embodiments of an eyewear include an eyewear without glasses, an auxiliary frame, and/or different types of glasses, such as sunglasses, fit-over glasses, prescription glasses, safety glasses, swim masks, and/or other types of goggles, such as ski goggles and diving goggles. While two lenses 160, 162 are depicted in FIG. 1, the electronic eyewear can include a single eye-piece forming glasses, which could be goggles. Further, embodiments of the frame 100 include a frame of glasses, a frame of goggles and a connecting piece between lenses of frameless glasses. Further, embodiments of the switches 130, 132 can be located between the frame 100 and the temple arms 110, 112, or between the at least one of the lens and the temple arms 110, 112. In yet another embodiment, temple arms of an electronic eyewear could be significantly shortened, and could be attached to a cord, or a band, such as a lanyard, which could be used to secure the eyewear to its wearer or user.

For an embodiment, the frontal plane includes an effective plane of the one or more lenses 160, 162. As shown, for an embodiment, at least one of the temple arms 110, 112 is rotatable about a point as determined by where the temple arm is connected (attached) to the eyewear. As a temple arm (such as, temple arm 110) is rotatably adjusted, an angle of the temple arm relative to the frontal plane (shown as angle 140) is varied. As shown in FIG. 1, for the position of the temple arm 110 relative to the frontal plane, and angle of temple arm relative to the frontal plane is approximately 80 degrees. For this embodiment, the angle can be adjusted between approximately 0 degrees to approximately 90 degrees.

In one embodiment, an eyewear includes a lens holder and two temples (which can also be known as temple arms), each temple connected to the lens holder via a hinge. Each temple could be folded in or extended out, based on its corresponding hinge. When a temple is fully folded in, the angle between the temple and the lens holder is substantially 0 degrees; and when the temple is extended out, in its typically stable condition, the angle between the temple and the lens holder is substantially 90 degrees. Note that for some eyewear, when a temple is urged to be fully extended out, the angle between the temple and the lens holder can be more than 90 degrees. In one embodiment, the angle between a temple and the lens holder is substantially the same as the angle 140 between a temple and the frontal plane as shown in FIG. 1.

In yet another embodiment, the frontal plane is substantially parallel to a back plane formed by the two hinges as previously described. For example, the back plane of a pair of glasses can be formed by placing the glasses with its lenses on its frontal plane, removing its temples and having a plane sitting on top of the two hinges. That plane can be the back plane.

For an embodiment, the at least one switch is located within at least one hinge formed between the frame and at least one of the pair of adjustable temple arms. As previously described, for an embodiment, the at least one hinge is formed between the at least one lens and at least one of the pair of adjustable temple arms.

For an embodiment, the at least one switch includes a spring mechanism that urges the at least one switch to be at least one of open or closed. For an embodiment, the at least one switch is located within at least one hinge formed between the one or more lenses and the pair of adjustable temple arms.

For an embodiment, the at least one switch is open or closed depending on whether the angle is less than or greater than X degrees. For an embodiment, X is approximately 80 degrees. For an embodiment, the at least one switch is closed if the angle is greater than X degrees, and open if the angle is less than X degrees. For an embodiment, the switches are electronic switches, and closing a switch enables an electronic current to be conducted through the switch, and opening the switch prevents an electronic current from being conducted through the switch.

For an embodiment, the at least one switch includes a first switch 130 located within a first hinge formed between the frame 100 and a first adjustable temple arm 110 of the pair of adjustable temple arms, and a second switch 132 located within a second hinge formed between the frame 100 and a second adjustable temple arm 112 of the pair of adjustable temple arms. For an embodiment, the first switch 130 is open or closed depending on whether a first angle (for example, angle 140) of the first hinge is less than or greater than X degrees, and the second switch 132 is open or closed depending on whether a second angle of the second hinge is less than or greater than Y degrees. For an embodiment, X is approximately equal to Y.

For an embodiment, the electronic eyewear includes a controller 150. The controller 150 of FIG. 1 is shown as being located between the viewing portions of the lenses (for example, between the lens 160 and the lens 162) which can be referred to as the bridge of the eyewear. However, the controller can be located in other area within the electronic eyewear.

For an embodiment, the controller 150 is operative to monitor a state of the electronic eyewear depending on whether the at least one switch is open or close. As described, if the switches are electronic switched, the switches are able to conduct current if close, and are not able to conduct current if opened. Therefore, the states (open or closed) can be sensed by electronic circuitry, and therefore, sensed or determined by the controller. For an embodiment, the monitored state comprises monitoring whether a user is wearing the glasses.

For an embodiment, the controller 150 is operative to monitor a state of the electronic eyewear by monitoring whether the first switch 130 is open or close and whether the second switch 132 is open or closed. For an embodiment, the monitored state comprises monitoring whether a user is wearing the glasses.

For an embodiment, the controller is operative to perform a command, wherein the command is determined based on whether the first switch is open or closed and whether the second switch is open or closed. For an embodiment, the command includes at least one of a system on/off command, a display functioning cycle-time, battery life display, an LCD frequency adjust, a reset. For an embodiment, a first command is performed if both the first switch and the second switch are closed, a second command is performed if the first switch is closed and the second switch is open, a third command is performed if the first switch is open and the second switch is closed, and a fourth command is performed if both the first switch and the second switch are closed. Clearly, fewer than four commands can be performed based on the state of the switches of the electronic eyewear.

For an embodiment, the controller 150 is operative to treat a patient with shutter glasses therapy for at least a relatively short period of time, such as a 6 week period; wherein the shutter glasses therapy includes blanking a first lens of shutter glasses being worn by the patient for a first blocking time, blanking a second lens of the shutter glasses being worn by the patient for a second blocking time, and controllably setting at least one of the first blocking time and the second blocking time. For an embodiment, the controller 150 is further operative to apply the shutter glasses therapy for 6-7 days for each of the at least 6 weeks. For an embodiment, the controller 150 is further operative apply the shutter glasses therapy for 1-2 hours for each day of the 6-7 days. For an embodiment, the controller 150 is further operative to monitor use of the shutter glasses by the patient. For an embodiment, the controller 150 is further operative to display the monitored use to the patient. For an embodiment, the controller 150 is further operative to provide an indicator to the patient when the patient has satisfied a therapy use. For an embodiment, the therapy use includes at least one of an hourly use, a daily use or a weekly use.

Figure 2:
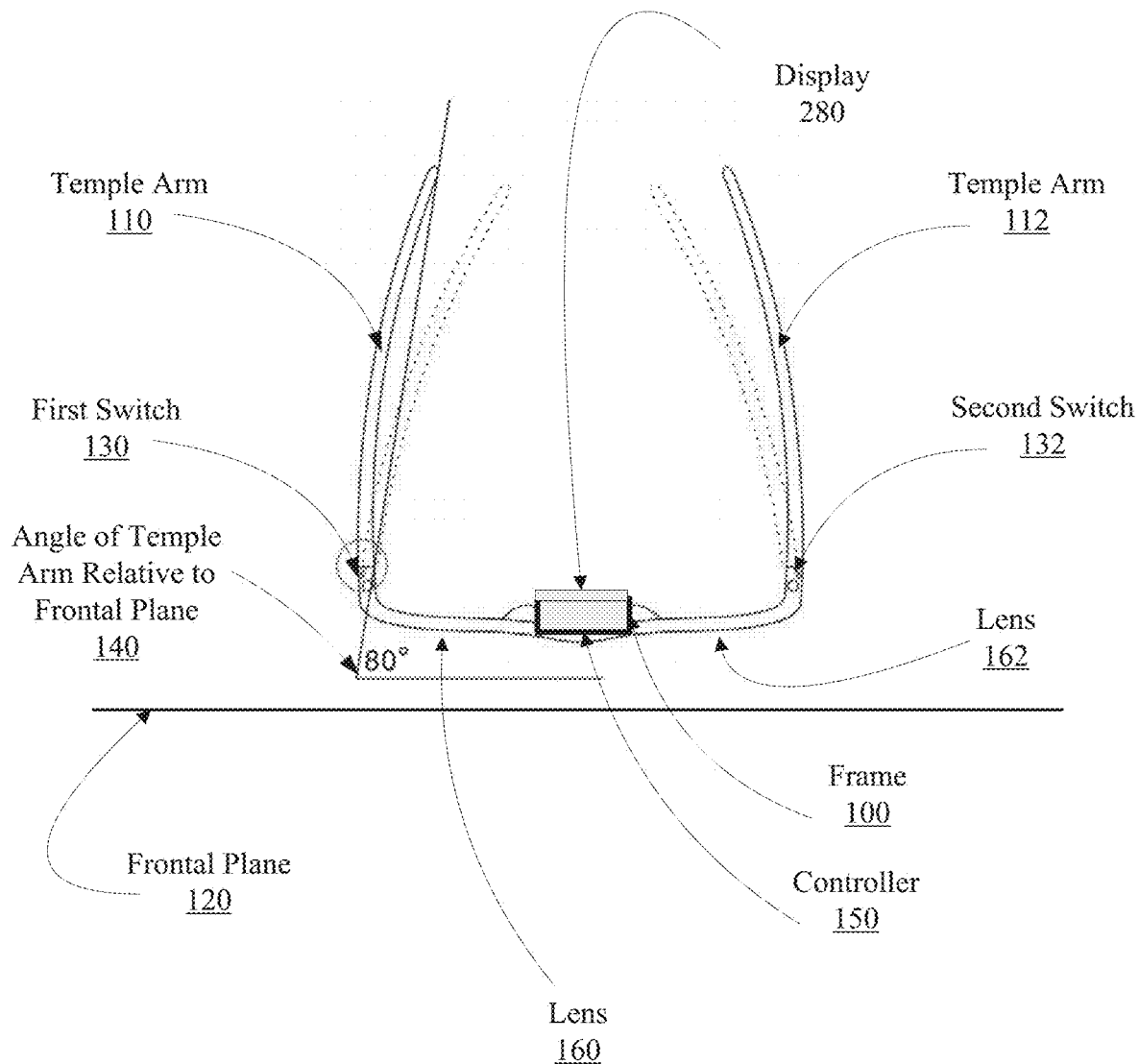
FIG. 2 shows another block diagram of electronic eyewear according to another embodiment.

FIG. 2 shows another block diagram of electronic eyewear according to another embodiment. This embodiment further includes a 280 display located on or within the electronic eyewear, such as at the bridge or other area of the eyewear. For an embodiment, the display provides information. For an embodiment, the information provided is controlled by the controller 150. For an embodiment, the information provided is controlled by a controller external to the eyewear. For an embodiment, the command includes providing an indicator of how long the user has worn the glasses. For an embodiment, the command includes providing an indicator of how long the user has worn the glasses for a given day. For an embodiment, the display is located between the lenses on a side of the frame that is adjacent to or facing the user's eyes when wearing the eyewear. For an embodiment, the display allows for providing an indicator to the patient when the patient has satisfied a therapy use. For an embodiment, the therapy use includes at least one of an hourly use, a daily use or a weekly use.

For an embodiment, the electronic eyewear further includes a battery, and the command includes providing an indicator of a remaining lifetime of the battery.

The display can be used, for example, by the user to monitor how long and/or frequently the user has been wearing the glasses. The user can thereby monitor whether the user is properly following usage of the electronic eyewear as prescribed, for example, by a doctor or therapist. Further, operational use of the electronic eyewear can be monitored, and then the results of the monitoring accessed by the user by providing command inputs to the controller, causing the controller to provide the results on the display for observation by the user.

Figure 3:
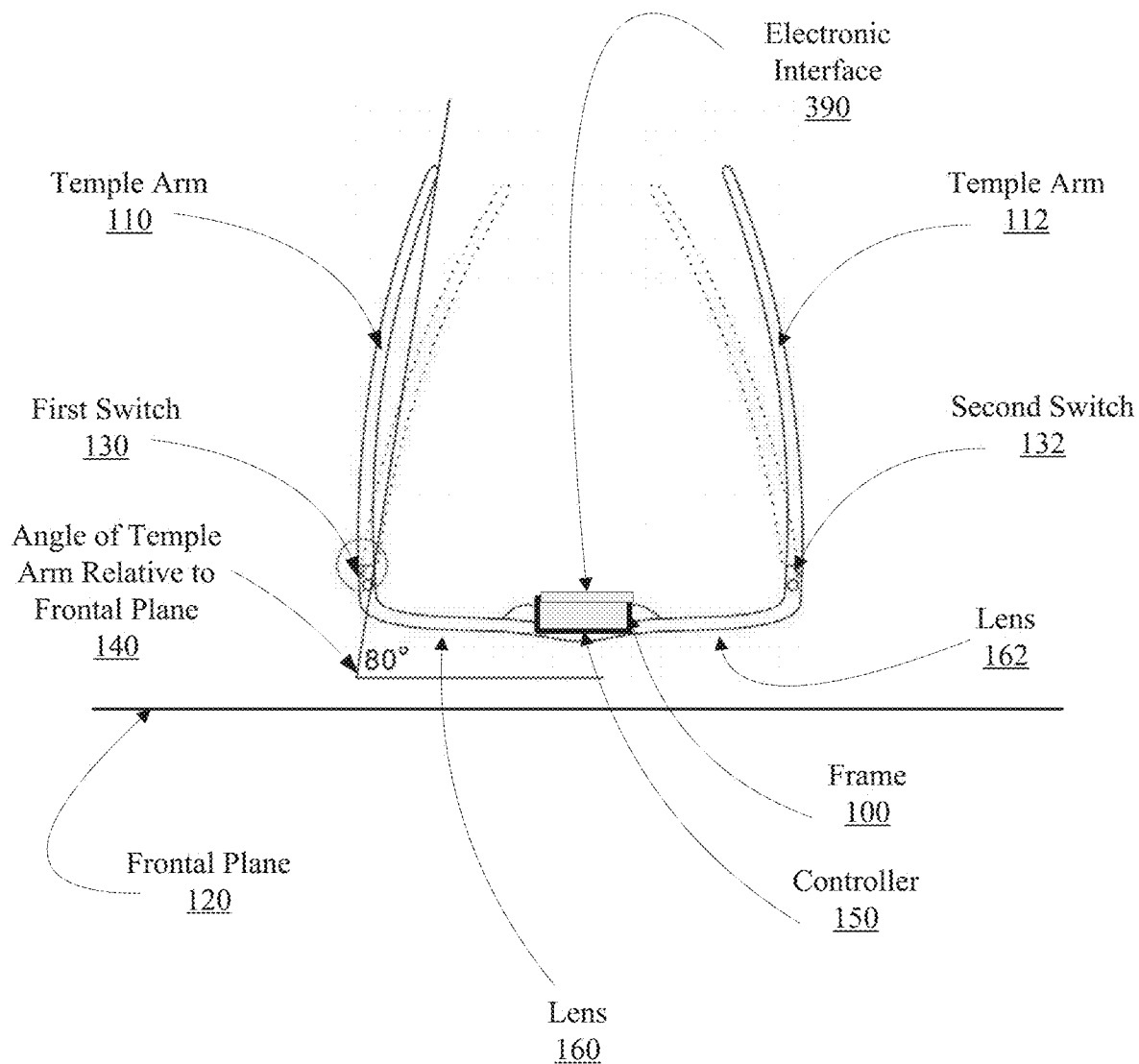
FIG. 3 shows another block diagram of electronic eyewear according to another embodiment.

FIG. 3 shows another block diagram of electronic eyewear according to another embodiment. This embodiment further includes an electronic interface 390, such as at the bridge or at other area of the eyewear. For an embodiment, the electronic interface 390 allows the controller 150 to upload monitored behavior of the user of the electronic eyewear. For example, the states of the switches 130, 132 can be used to monitor whether the user has been wearing the electronic eyewear, and for how long. This is useful, for example, when a therapist or doctor is treating the eyes of the user. The therapist or doctor can access the monitored behavior of the user as stored in memory of the electronic eyewear. For an embodiment, the electronic interface is a wired interface that provides communication between the controller 150 and the external controller. For an embodiment, the electronic interface includes a wireless interface (wireless transceiver) and provides a wireless connection between the controller 150 and an external controller. For an embodiment, the controller 150 transmits and/or receives information (including commands) with a second (external) controller. The communication allows configuring the glasses (frequencies etc.) to be done remotely through a wireless network, such as a Bluetooth or Wifi network, via a portable device, such as IPad.

Figure 4:
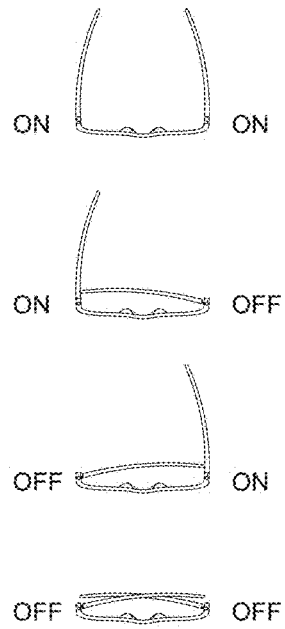
FIG. 4 shows four different states of the electronic eyewear as determined by states of the switches of the electronic eyewear according to an embodiment.

FIG. 4 shows four different states of the electronic eyewear as determined by states of the switches of the electronic eyewear according to an embodiment. That is, for this embodiment, a first state includes both switches closed, a second state include one switch close and one switch open, a third state includes the one switch open and one switch closed, and a fourth state include both switches open.

As shown in FIG. 4, the four states provided by opening or closing the switches of the electronic eyewear can be used as commands for the controller within the electronic eyewear. The commands can include, for example, a system on/of command, a display of the functioning cycle-time, a battery life, an adjustment to the shuttering frequency of the LCD lenses of the electronic eyewear, and/or a reset command.

Figure 5:
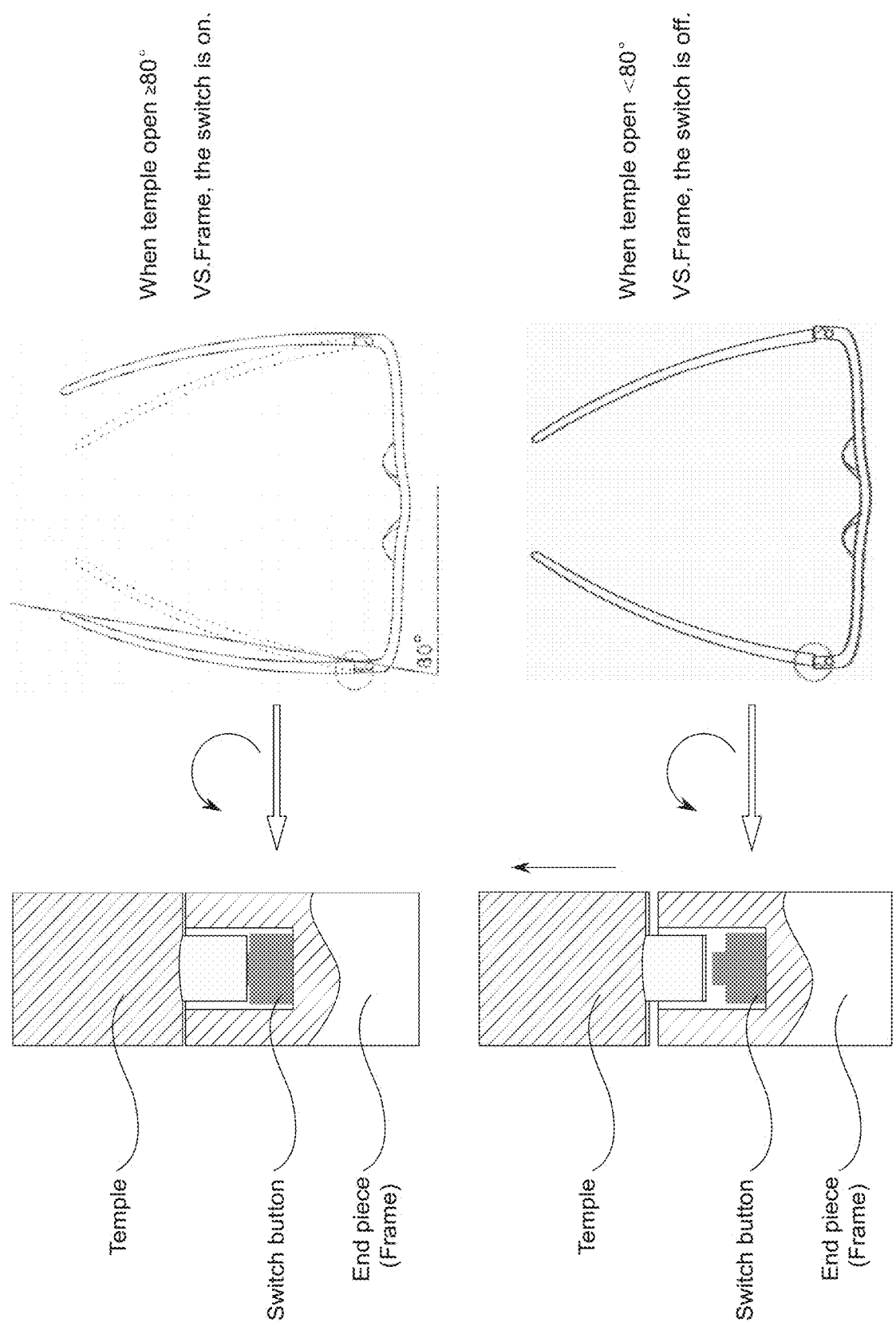
FIG. 5 shows an electronic switch of the electronic eyewear according to an embodiment.

FIG. 5 shows an electronic switch of the electronic eyewear according to an embodiment. The electronic switch includes a switch button that is closed when the angle of at least one of the corresponding temple arms relative to a frontal plane of the lenses exceeds a predetermined angle.

Figure 6:
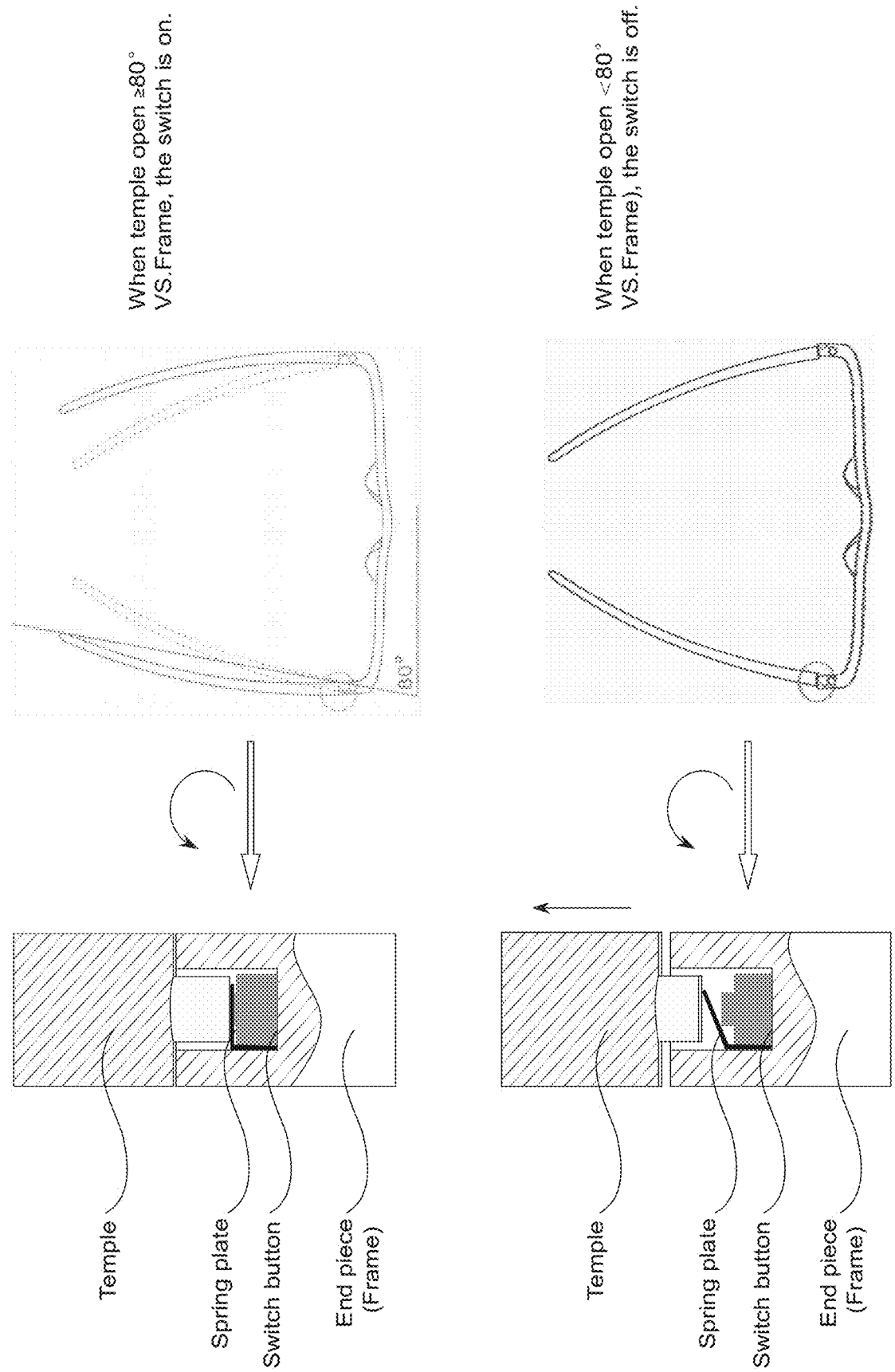
FIG. 6 shows another electronic switch of the electronic eyewear according to another embodiment.

FIG. 6 shows another electronic switch of the electronic eyewear according to another embodiment. The electronic switch includes a spring mechanism and a switch button that is closed when the angle of at least one of the corresponding temple arms relative to a frontal plane of the lenses exceeds a predetermined angle.

Figure 7:
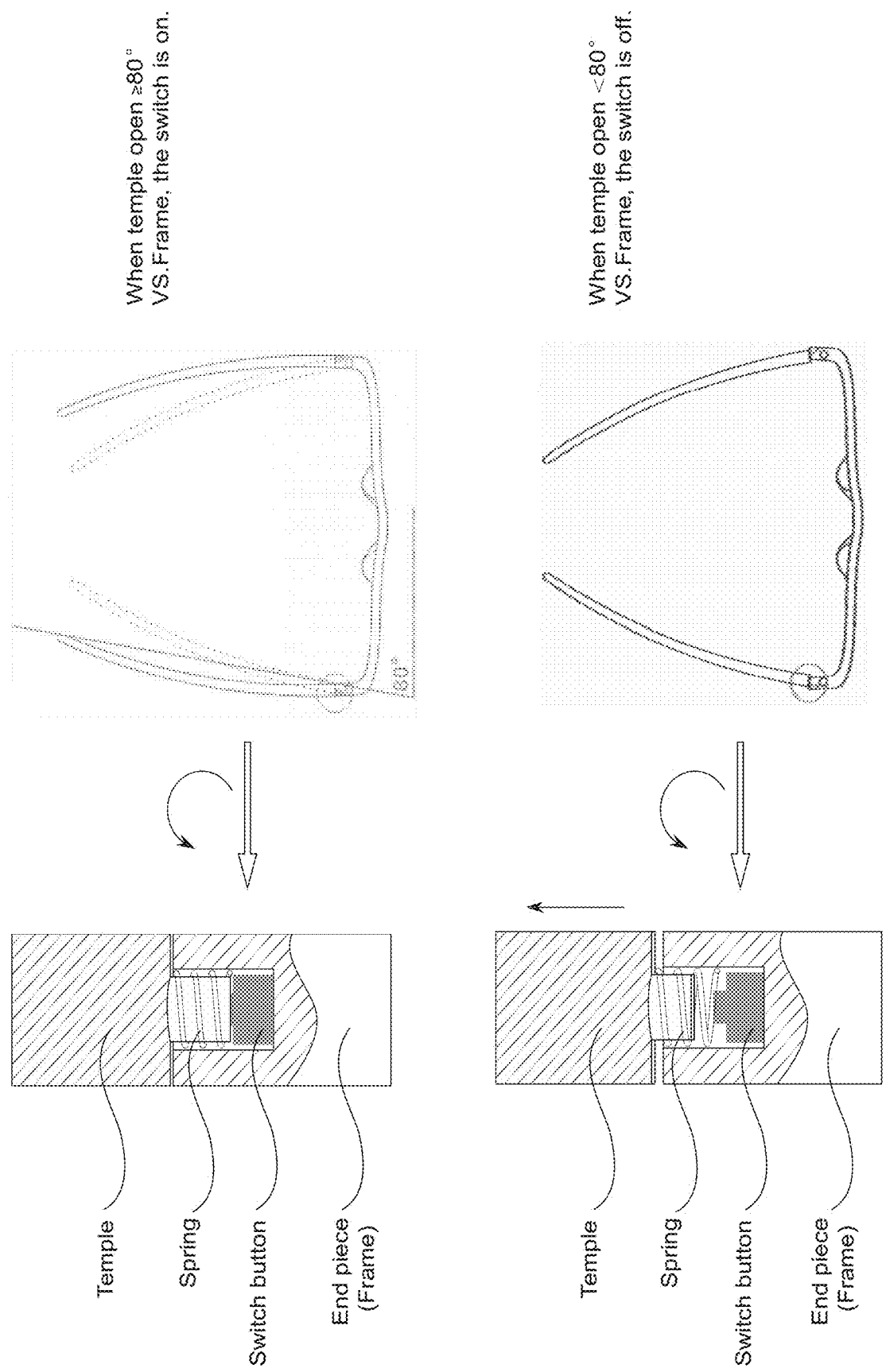
FIG. 7 shows another electronic switch of the electronic eyewear according to another embodiment.

FIG. 7 shows another electronic switch of the electronic eyewear according to another embodiment. The electronic switch includes a spring mechanism and a switch button that is closed when the angle of at least one of the corresponding temple arms relative to a frontal plane of the lenses exceeds a predetermined angle.

Figure 8:
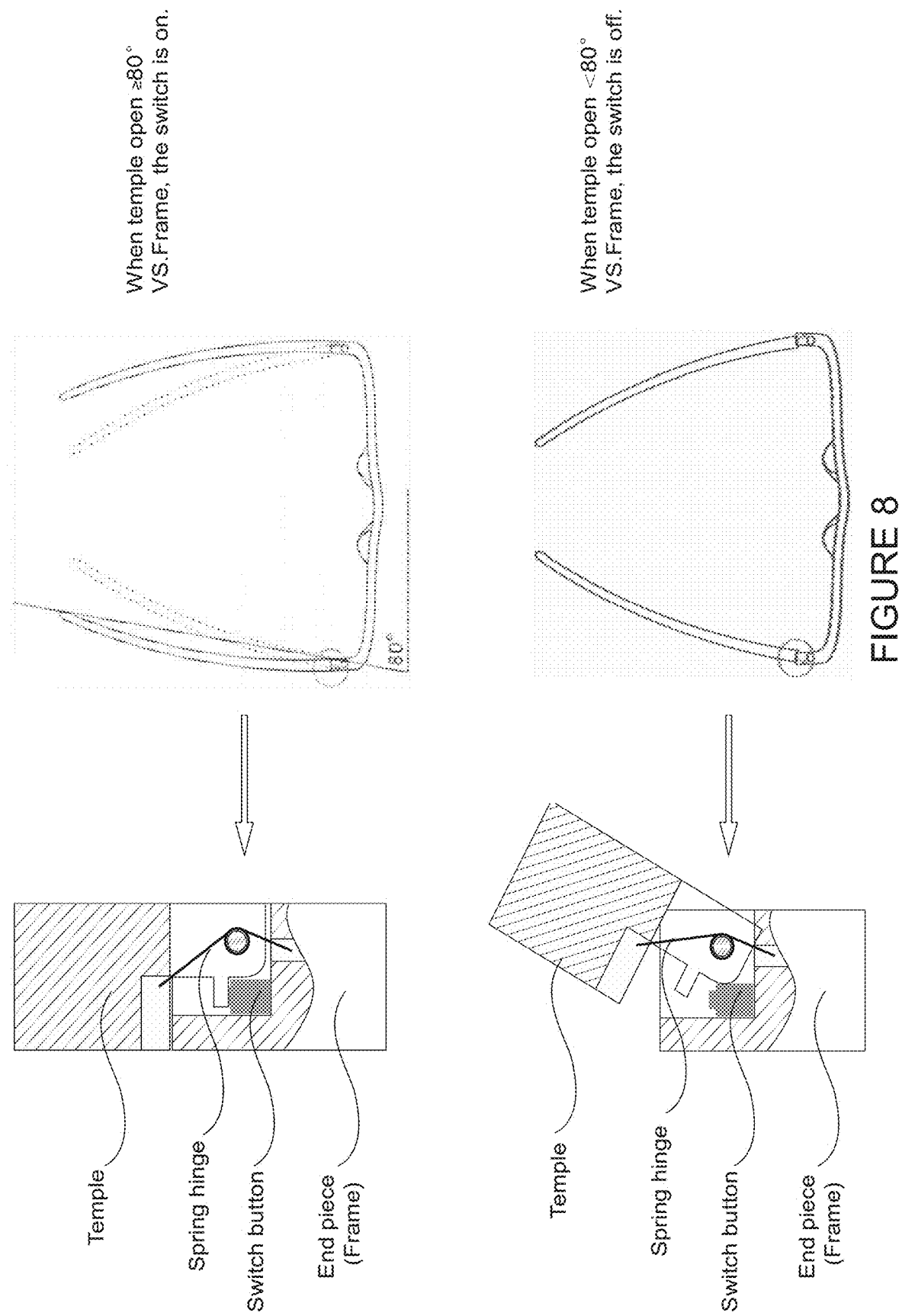
FIG. 8 shows another electronic switch of the electronic eyewear according to another embodiment.

FIG. 8 shows another electronic switch of the electronic eyewear according to another embodiment. The electronic switch includes a spring mechanism and a switch button that is closed when the angle of at least one of the corresponding temple arms relative to a frontal plane of the lenses exceeds a predetermined angle.

Figure 9:
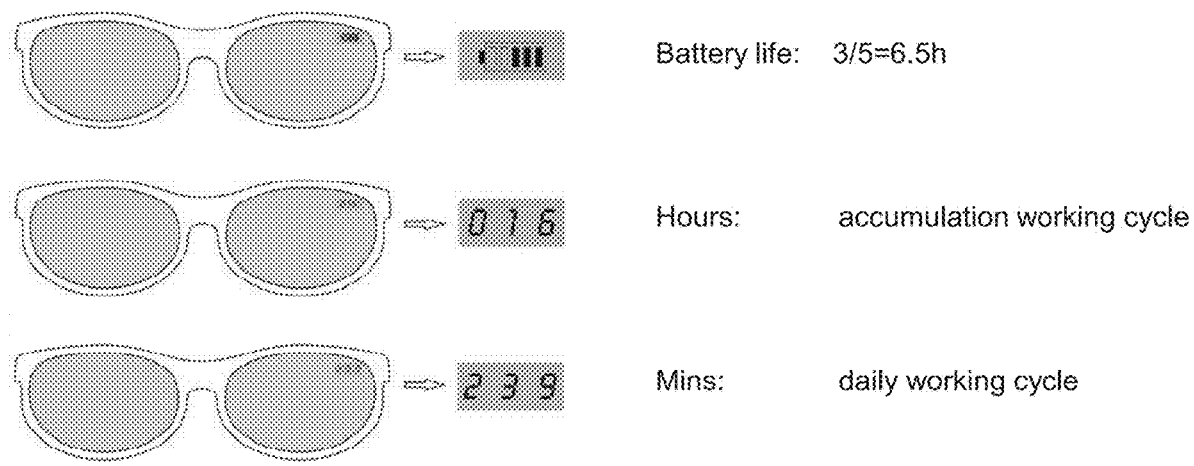
FIG. 9 shows an embodiment of a display which displays operational use information of the electronic eyewear according to an embodiment.

FIG. 9 shows an embodiment of a display which displays operational use information of the electronic eyewear according to an embodiment. The embodiment includes the display being located on a lens. However, it is to be understood that the display could be located at other areas of the eyewear, such as at an inside surface of a temple. For an embodiment, the display is on another device, such as, an external controller that can be interfaced wirelessly or wired with the electronic eyewear. Exemplary displayed information includes battery life (of a battery of the electronic eyewear), accumulation working cycle (which depicts the accumulated hours of wear of the electronic eyewear during period of time, such as, since a last session with a doctor), and a daily working cycle (which depicts, for example, the number minutes the electronic glasses have been worn during a current day).

Figure 10:
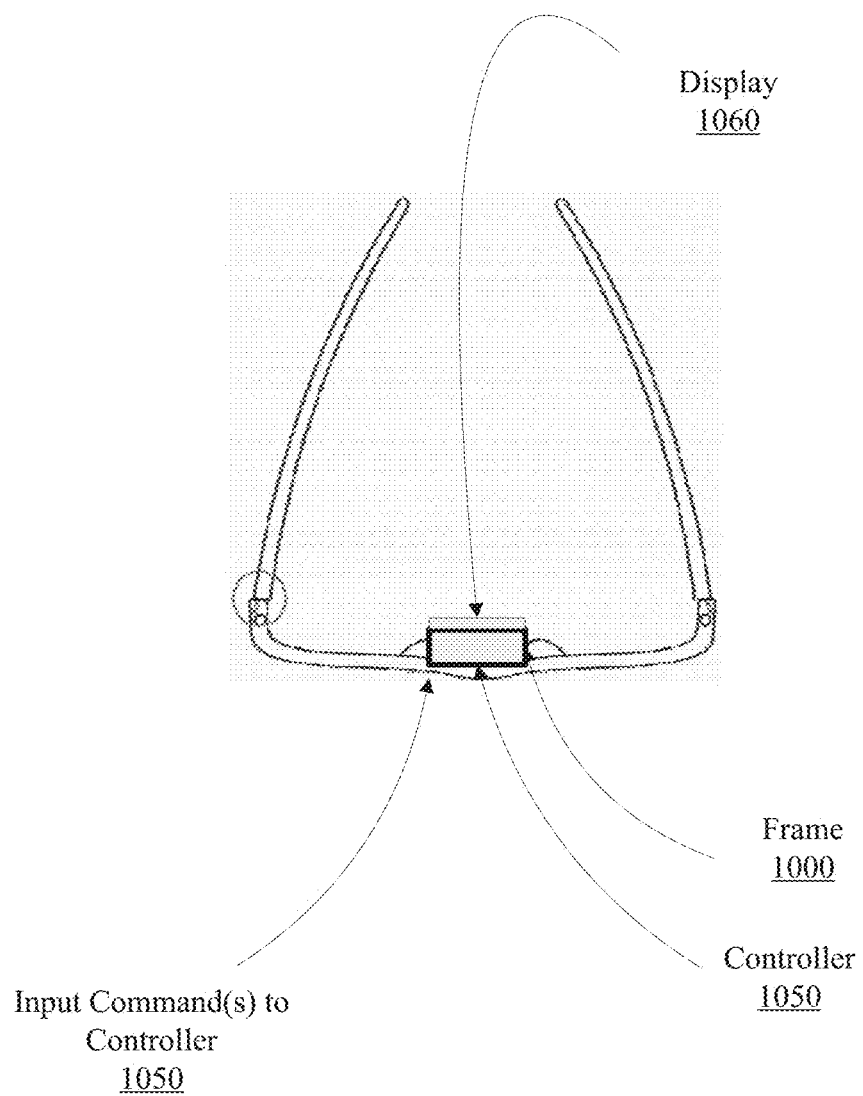
FIG. 10 shows another block diagram of electronic eyewear according to another embodiment.

FIG. 10 shows another block diagram of electronic eyewear according to another embodiment. This embodiment includes a frame 1000, a controller 1050 and a display 1060. This embodiment more generally shows the electronic eyewear in which the controller 1050 receives one or more commands from one of many different possible sources. For an embodiment, the controller 1050 receives the one or more command from one or more physical switch located on the electronic eyewear. For another embodiment, the controller 1050 receives the one or more command from one of the previously described physical switch located at the hinges of the electronic eyewear. For an embodiment, the controller 1050 receives the commands from an external controller through an electronic interface of the electronic eyewear. For an embodiment, the controller 1050 receive one or more commands, and displays a use parameter of the eyewear on the display 1060 based on the one or more received commands.

For an embodiment, the use parameter includes timing of how long the eyewear has been worn by a user. For an embodiment, the use parameter includes when the eyewear has been worn by a user. For an embodiment, the use parameter includes a battery life of the eyewear.

The use parameter provides a user or a doctor with information related to the use of the glasses. The user parameter is not merely an indication of a setting provided to the electronic eyewear. For one embodiment, the use parameter provides a user or a doctor with information related to the use of the glasses.

For an embodiment, the display 1060 is located between the lenses on a side of the frame 1000 that is adjacent to a user's eyes when wearing the eyewear. For an embodiment, the one or more commands are received from an external controller. For an embodiment, the one or more commands are received from one or more switches located on the frame. For an embodiment, the electronic eyewear includes a pair of temple arms, and at least one switch, wherein the at least one switch is open or closed depending upon an angle of at least one of the temple arms relative to a frontal plane of the one or more lenses. For an embodiment, the one or more command are received from the at least switch based on whether the at least one switch is open or closed. For an embodiment, at least one switch includes a first switch and a second switch, wherein each switch is open or closed depending upon an angle of at least one of the temple arms relative to a frontal plane of the one or more lenses.

One of the described embodiments encourages the use of both eyes simultaneously so that the brain does not suppress input from one eye. Another embodiment forces an amblyopic eye to work harder.

In one embodiment, the lenses of an eyewear, such as a pair of glasses, could be LCD lenses.

One embodiment shutters the two lenses by alternately blanking the left and the right lens back and forth. For example, the shuttering speed of the lenses can be adjusted. This can be done, for example, by a knob, a slider or a small dial on the corresponding frame to program the frequency of the blanking. The switching speed can range from a few milliseconds to a short number of seconds. In another example, the switching frequency can range from 1 Hz to 15 Hz (such as in 1 Hz increment). In yet another example, the switching frequency can range from 6 to 10 Hz (such as in 0.5 Hz increment).

In another embodiment, the duty cycle of the blanking of the left and the right lens during the switching can be controlled. For example, their phase relationship can be 90 degrees, or at some other degrees. In another example, an amblyopic eye can be forced to work harder by having its corresponding lens turned on longer than the other lens. In yet another example, the shutter lenses can have different blocking times for each lens depending on which eye is more dominant or lazy.

An embodiment includes the application of a course therapy to a user (patient) wearing the electronic eyewear. For an embodiment, the course therapy includes an external computer, or the controller of the electronic eyewear automatically selected a blanking frequency, or a sequence of blanking frequencies. The selected blanking frequency or sequence of blanking frequencies can be automatically selected based on the condition of the user. The selected blanking frequency or sequence of blanking frequencies can be based on the identification of trends of responses observed from past users/patients. The selected blanking frequency or sequence of blanking frequencies can be identified as being successful or not based on testing/use with past users/patients.

Further, the blanking frequency or the sequence of blanking frequencies is applied to the shuttering eyewear of the user. For an embodiment, a physician observes the patient while the sequence of blanking frequencies is applied to the shuttering eyewear of the user. The physician can maintain the present setting, or based on monitoring or observation, or the physician can adjust the blanking frequency or sequence of blanking frequencies being applied to the patient. In some situations, a patient's mind can fatigue to an applied blanking frequency, and the blanking frequency is no longer effective. For an embodiment, the blanking frequency is changed to reduce or eliminate the effects of the fatigue.

An embodiment of the electronic eyewear is able to identify that a user/patent has developed a fatigue to a previously selected blanking frequency or the sequence of blanking frequencies. The electronic eyewear can then automatically modify the blanking frequency or the sequence of blanking frequencies to mitigate the effects of user/patient fatigue to the previously selected blanking frequency or the sequence of blanking frequencies.

In one embodiment, the different attributes of the shutter lenses can be programmable via switches (such as the previously described switches) on the corresponding frame or wirelessly via a remote control.

In one embodiment, the shutter lenses with the corresponding control circuitry and power source can be in a secondary frame, which is attachable to a primary frame via different mechanisms, such as magnets.

In one embodiment, the shutter lenses with the corresponding control circuitry and power source can be in a fit-over frame that can fit over another frame.

In one embodiment, the shutter lenses can be integrated into prescription lenses providing focal correction, such as bi-focal, tri-focal, prism, etc.

In one embodiment, the shutter lenses can auto-modulate to provide shading capability when used in sunny areas while still providing alternating vision blocking as described above.

In one embodiment, the shutter glasses are rechargeable or include power sources, such as a battery, to allow the glasses to perform its operation over a duration of time, such as a few hours.

In one embodiment, the shutter glasses may be secured from the back with a functional strap, such as a lanyard, that may contain the control circuitry and power source. This can provide additional ergonomic qualities and securing for active patients.

In one embodiment, the shutter glasses can be marketed to optometrists and ophthalmologists.

In yet another embodiment, the shutter frequency for the two lenses can be independently controlled.

Figure 11:
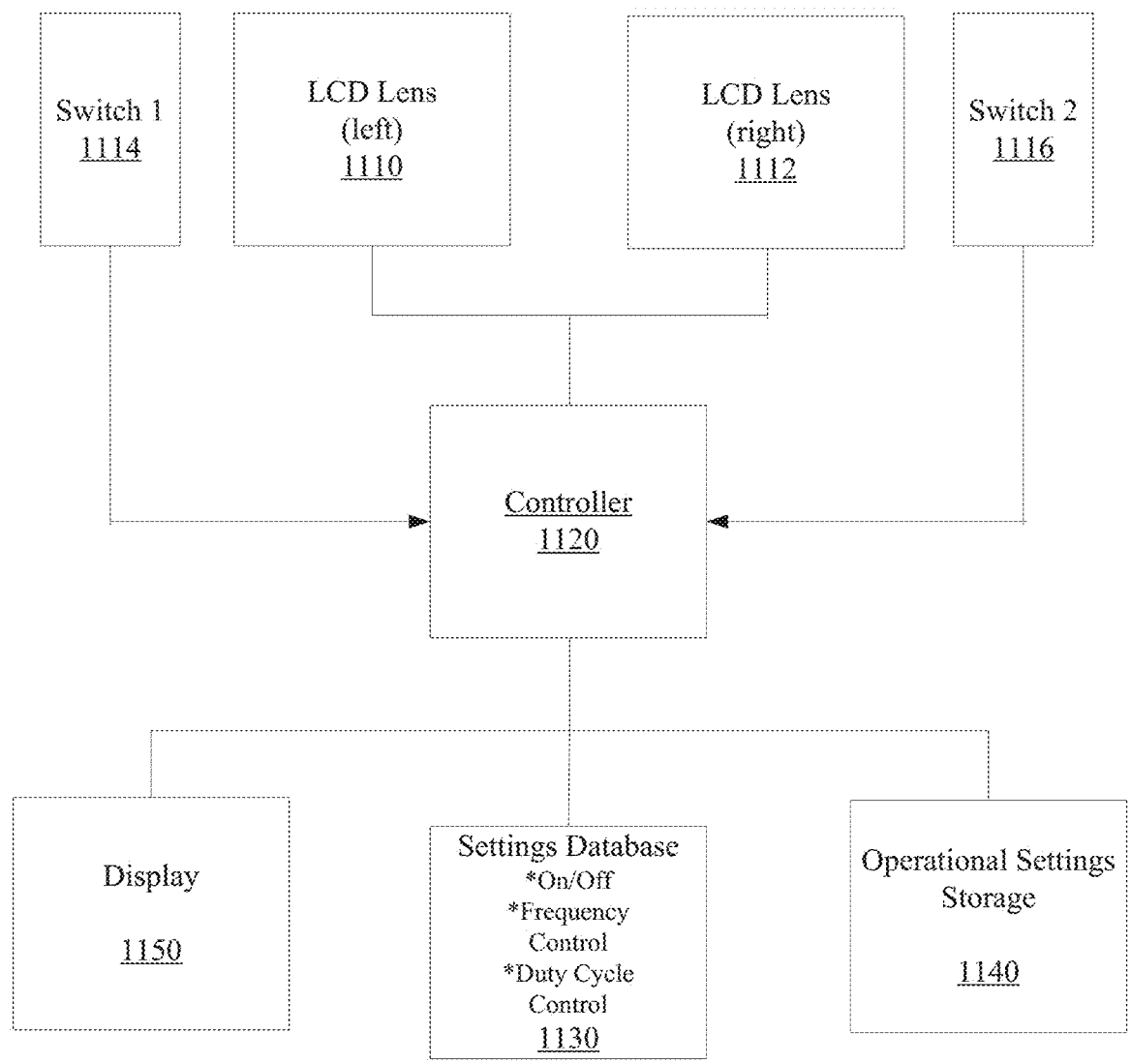
FIG. 11 shows a block diagram of electronic shutter glasses according to another embodiment.

FIG. 11 shows a block diagram of electronic shutter glasses according to an embodiment. As shown, this embodiment of the shutter glasses includes a left lens 1110 and a right lens 1112. For an embodiment, the left lens 1110 and the right lens 1112 include LCD lenses.

For an embodiment, a controller 1120 provides control of at least one of frequency or blocking period (blocking time) of at least one of the first lens 1110 or the second lens 1112. For an embodiment, the left lens 1110 is operable to blank for a first blocking time, the right lens is operable to blank for a second blocking time, and the controller 1120 controllably sets at least one of the first blocking time and the second blocking time. For an embodiment, the control of at least one of frequency or blocking period is adjustable. For an embodiment, the control of the first lens 1110 is independent of the control of the second lens 1112. For an embodiment, the controller 1120 is at least partially controlled by switches 1114, 1116 that provide at least one of on/off control, frequency control, and/or duty cycle control. For an embodiment, a database 1130 includes selections for blanking frequency and duty cycle control. As previously described, the blanking frequency and duty cycle control can be updated as a patient develops fatigue to selected blanking frequencies and duty cycles. Further, the selected blanking frequency and duty cycle control can include sequences of blanking frequency and duty cycle control. For an embodiment, the frequency of the shuttering (switching from a non-block condition or state to a blocking condition or state) is the same for both lenses, but the blocking time or duty cycle of one lens is different than the blocking time or duty cycle of the other lens, thereby forcing one eye of a user to work harder than the other eye.

For an embodiment, the controller 1120 is operable to access operational settings of at least the frequency and/or duty cycle from operational setting storage 1140. For an embodiment, the operational settings can be adaptively updated depending upon an eye ailment a user of the shutter glasses is suffering from. Additionally, for an embodiment, the storage 1140 is used for storing monitoring information that can be accessed.

For an embodiment, at least one of the first switch 1114 or the second switch 1116 is operational to provide commands to the controller 1120.

For an embodiment, a display 1150 provides use information of the electronic glasses. For an embodiment, the information of the display is provided by the controller 1120 as commanded by the first switch 1114 or the second switch 1116.

Figure 12:
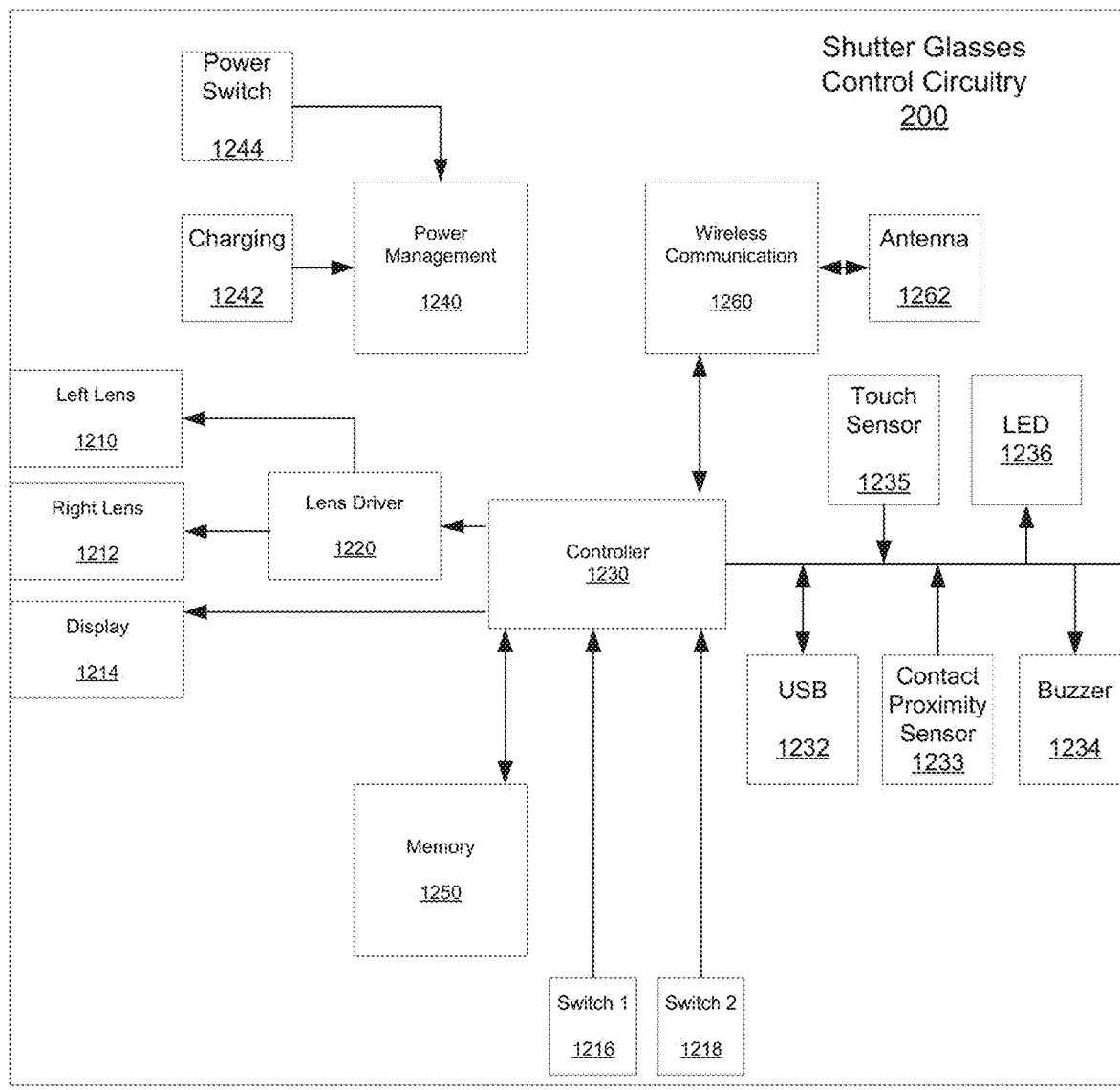
FIG. 12 shows a block diagram of electronic shutter glasses according to another embodiment.

FIG. 12 shows a block diagram of electronic shutter glasses according to another embodiment. This embodiment provides examples of different types of functionality that can be included with the shuttering glasses control circuitry 1200.

An embodiment includes a controller 1230 that controls at least one of frequency or blocking times of at least one of a left lens 1210 and a right lens 1212. The controller 1230 can interface with an external controller.

For an embodiment, the controller 1230 interfaces with a lens driver 1220 that drives states of the left lens 1210 and the right lens 1212. For an embodiment, the lenses 1210, 1212 include LCD lenses. Accordingly, for this embodiment, the lens driver is an LDC lens driver.

For an embodiment, the states of the left lens 1210 and the right lens 1212 include a blocking state (the lens being opaque and not letting light pass through) and a non-blocking state (the lens being transparent and letting a majority of light pass through). An embodiment includes intermediate states that allow varying amount of light pass through the lenses depending upon the intermediate state. The process of blanking includes the lenses alternating between blocking and non-blocking.

For an embodiment, the controller 1230 interfaces with memory 1250. For an embodiment, the controller 1230 accesses from the memory 1250 stored operational modes of the states of the left lens 1210 and the right lens 1212. For an embodiment, the controller 1230 stores operational information of the shuttering glasses in the memory 1250 for future access. For an embodiment, the operational information includes user usage of the shuttering glasses. For an embodiment, the operational information includes monitored or collected information of the user. The monitored information can be access by an external controller, thereby allowing determination of compliance by the user of the shutter glasses. That is, compliance by the user properly wearing the shutter glasses for a prescribed duration of time can be determined by accessed storage of wearing times and patterns by the user of the shutter glasses.

An embodiment includes power management 1240 of the shuttering glasses. For an embodiment, the shuttering glasses include a battery. For an embodiment, a charging unit 1242 controls charging of the battery. An embodiment includes a power switch 1244. For an embodiment, the power management 1240 provides and distributes electrical power to, for example, at least one of the lens driver 1220, the controller 1230, the memory 1250, wireless communication circuitry, a touch sensor 1235, an LED (light emitting diode) 1236, a USB (universal serial bit) interface 1232, a contact sensor 1233 and/or a buzzer 1234.

An embodiment includes wireless communication circuitry 1260 that allows the controller 1230 to communicate with an external controller. For an embodiment, wireless communication circuitry 1260 is two-way in that the controller 1230 can either provide the external controller with information, or the controller 1230 can receive information from the external controller. An embodiment further includes an antenna 1262 for enabling the wireless communication. The wireless communication can be continuous or intermittent.

An embodiment includes the touch sensor 1235. For an embodiment the touch sensor 1235 allows a user to communicate with the controller 1230. For an embodiment, the touch sensor 1235 allows the controller 1230 to monitor the user of the shutter glasses.

An embodiment includes the LED 1236. For an embodiment, the LED 1236 allows the shutter glasses to provide visual communication to, for example, the user. For an embodiment, the LED 1236 provides a visual indicator that the shutter glasses have electrical power indicating, for example, that the shutter glasses are electrically turned on.

An embodiment includes the USB port 1232 for providing wired communication to or from the controller 1230. For example, an external controller can communicate with the controller 1230 through the USB port 1232.

An embodiment includes the contact/proximity sensor 1233. For an embodiment, the contact/proximity sensor 1233 provides an indication that the shutter glasses are being worn. For an embodiment, the controller 1230 monitors the usage (wearing of the shutter glasses) based on the contact/proximity sensor 1233.

An embodiment includes the buzzer 1234. For an embodiment, the buzzer 234 provides audible communication to, for example, the user. For an embodiment, the buzzer indicates to the user that the battery is low. For at least some embodiments, the buzzer is used to provide guidance to the user. For example, the buzzer can provide an indicator to the user to either take off or put the shutter glasses on.

For an embodiment, at least one of a first switch 1216 or a second switch 1218 is operational to provide commands to the controller 1230.

For an embodiment, a display 1214 provides use information of the electronic glasses. For an embodiment, the information of the display is provided by the controller 1230 as commanded by the first switch 1216 or the second switch 1218.

Figure 13:
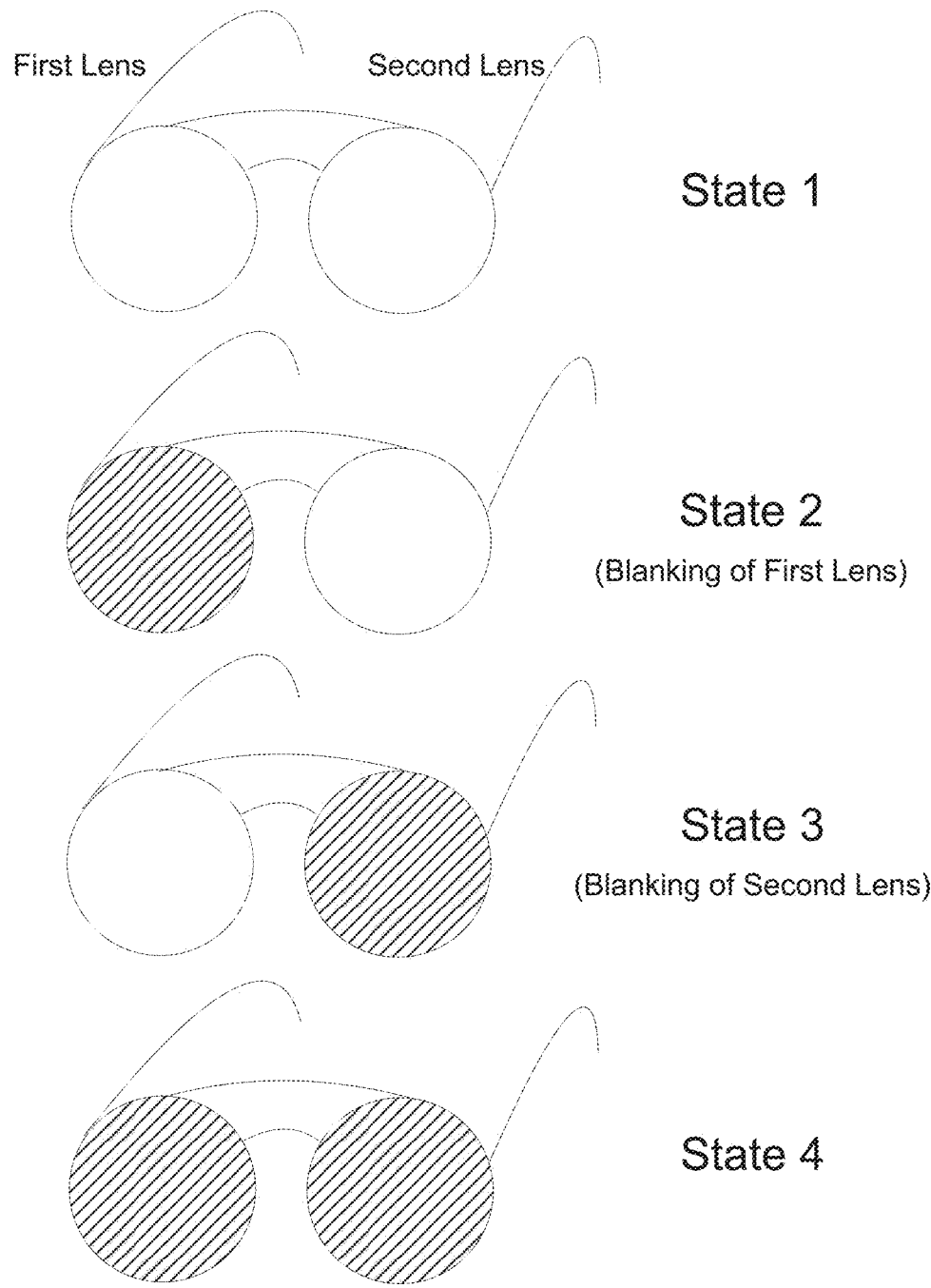
FIG. 13 shows shutter glasses in different states of operation according to an embodiment.

FIG. 13 shows shutter glasses in different states of operation according to an embodiment. As shown, an embodiment includes a first state wherein both a first lens and a second lens are in non-blocking. For an embodiment, a second state includes one lens (for example, the first lens) being in the blocking state, and the other lens (for example, the second lens) being in the non-blocking state. For an embodiment, a third state includes the other lens (such as, the second lens) being in the blocking state, and the lens (such as, the first lens) being in the non-blocking state. For an embodiment, a fourth state includes both lenses being in the blocking state. As described, at least some embodiments include controlling at least one of a frequency of the change from one state to at least one of the other states, or a blocking period (and conversely, the non-blocking period) of one or more of the states.

Figure 14:
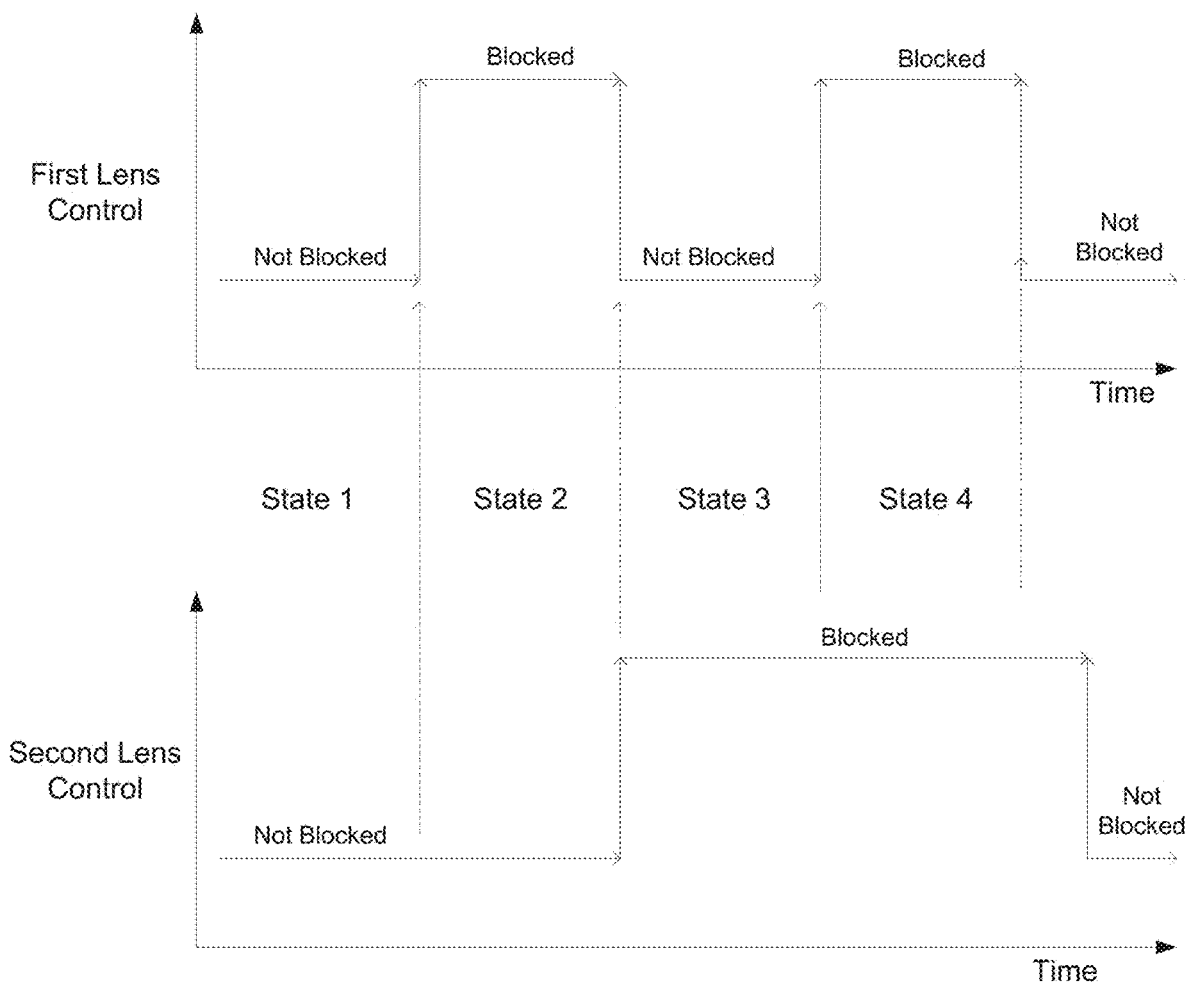
FIG. 14 shows time-lines of operation of the shutter glasses for the different states shown in FIG. 3, according to an embodiment.

FIG. 14 shows time-lines of operation of the shutter glasses for the states shown in FIG. 13, according to an embodiment. A first time line shows control of the first lens over time between being non-blocked and blocked. A second time line shows control of the second lens over time between being non-blocked and blocked. The four possible states of FIG. 13 are shown by the time-lines of FIG. 14 according to an embodiment.

Figure 15:
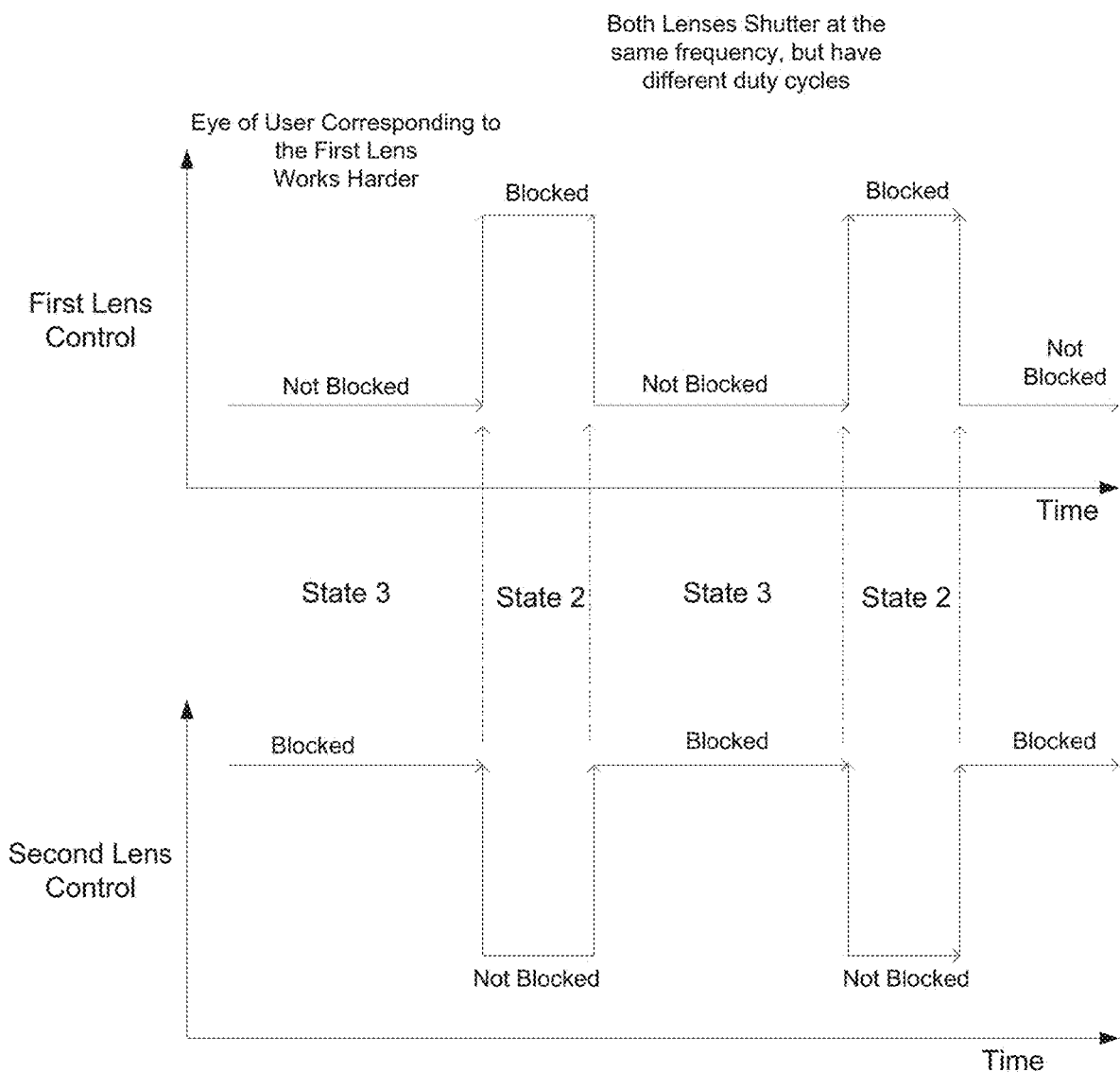
FIG. 15 shows time-lines of operation of the shutter glasses for the different states shown in FIG. 3, according to another embodiment.

FIG. 15 shows time-lines of operation of the shutter glasses for the states shown in FIG. 13, according to another embodiment. This embodiment includes the blocking period of the first lens being less than the blocking period of the second lens while alternately blanking (blocking) the left and the right lens back and forth. For this embodiment, the frequency of the shuttering of both lenses is approximately the same. The second lens is blocking for a greater percentage of a period of the frequency of the shuttering than the first lens. Accordingly, a user of the shutter glasses is forced to use vision of the eye that corresponds with the first lens a greater percentage of time. By blocking an eye (through blanking the corresponding lens) the shutter glasses force the brain of the user to switch over to the other eye. That eye (corresponding to the lens not being blanked) is forced to align properly to see the same target of interest, and the brain continues to use that eye until he cycle repeats and switches to the other eye. The shuttering causes the user of the shutter glasses to experience a combination of muscle alignment training and anti-suppression therapy.

Figure 16:
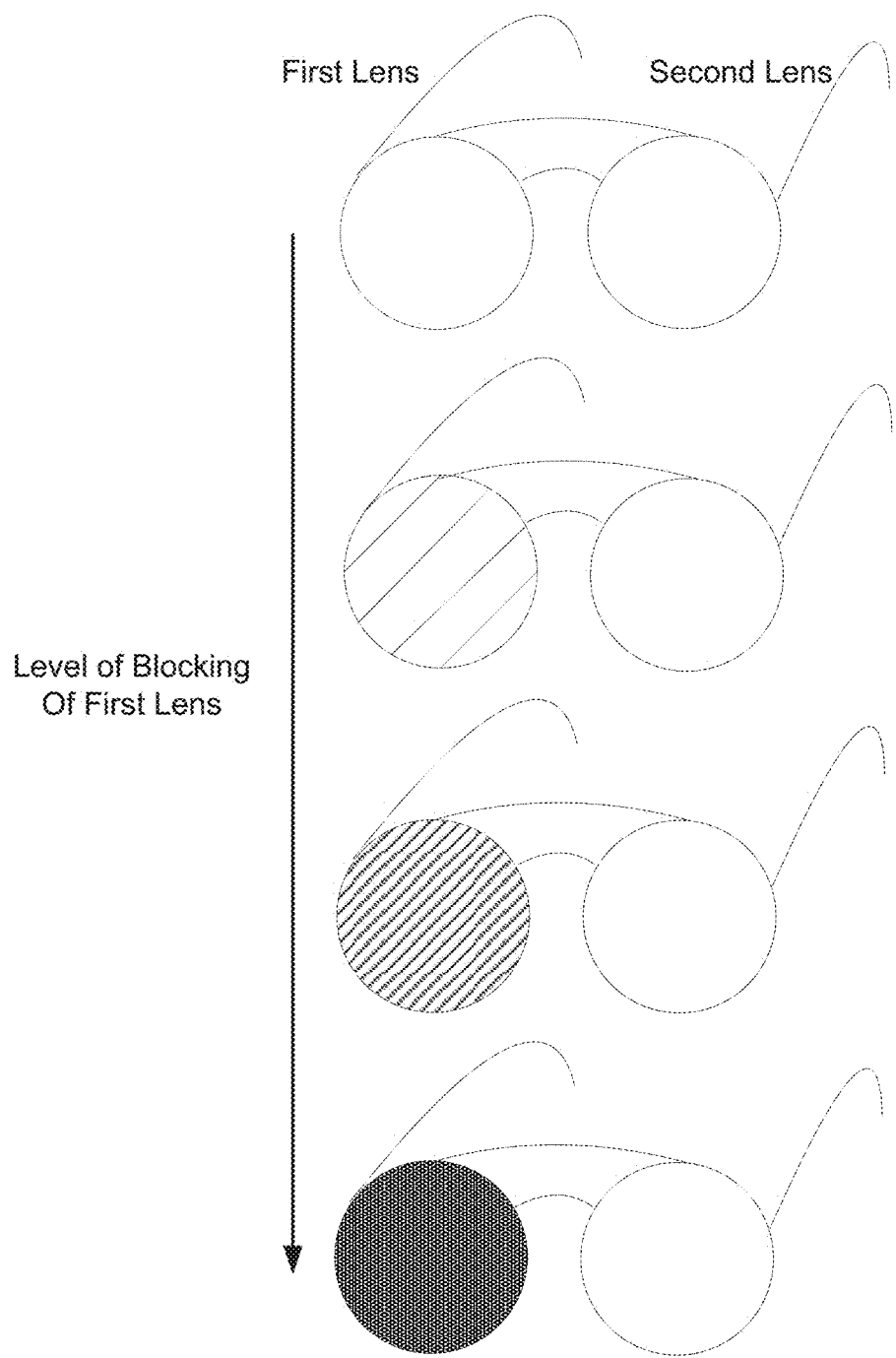
FIG. 16 shows shutter glasses that include an adjustable level of blocking, according to an embodiment.

FIG. 16 shows shutter glasses that include an adjustable level of blocking, according to an embodiment. For an embodiment, the level or degree of blocking of either of the lenses is adjustable. That is, the amount of light that passes through at least one of the shuttering glasses lenses is adjustable. FIG. 16 shows the first lens of the shuttering glasses, wherein the level or degree of the blocking is adjusted from near-transparent to near-opaque, with intermediate levels or degrees of blocking in between. For at least some embodiments, the level of blocking can be increased slowly or rapidly, and then the blocking can be independently decreased slowly or rapidly. Therapy being applied to the user of the shutter glasses can dictate how to control the blocking and the levels of blocking of either lens.

At least one embodiment includes adjusting the level according to any desired sequence. For example, the level of block can be increased or decreased as desired or programmed. The level of blocking of either lens can be dependently or independently controlled.

For an embodiment, the partial blocking of a lens includes block portions of the lens, wherein the portion is selectable.

Figure 17:
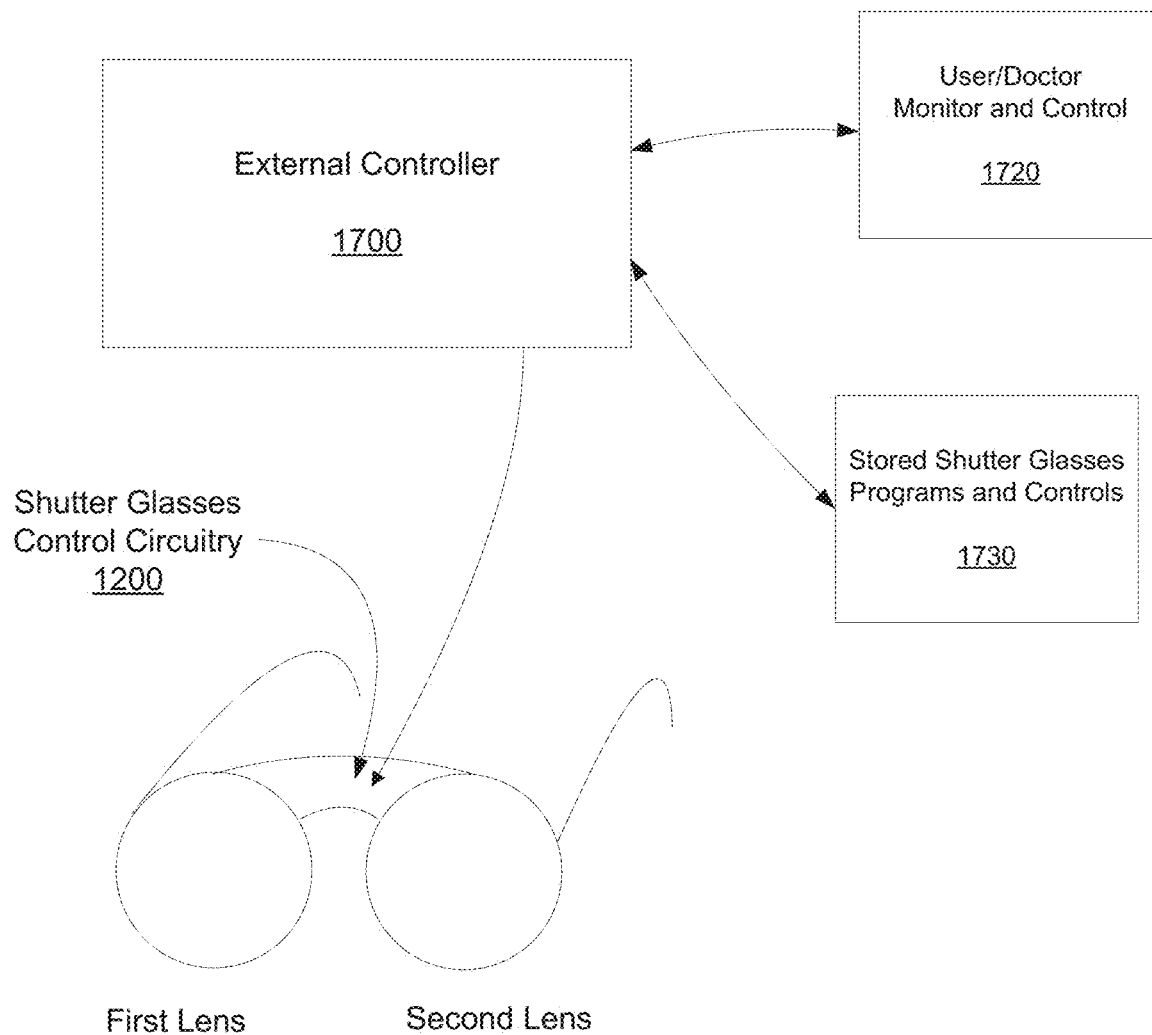
FIG. 17 shows shutter glasses interfaced with an external controller, according to an embodiment.

FIG. 17 shows shutter glasses interfaced with an external controller, according to an embodiment. For an embodiment, shuttering glasses control circuitry 200 is operable to communicate, for example, with an external controller 1700. For an embodiment, the external controller allows a user or a doctor to monitor (1720) the usage of the user. For an embodiment, the user or the doctor is able to program the shuttering glasses through the external controller 1700. For an embodiment, the user or doctor can retrieve stored shuttering glasses program and controls 1730. Accordingly, the doctor can proscribe therapy by programming the shutter glasses. Additionally, the doctor can monitor the use of the shutter glasses by the user (patient), thereby allowing the doctor to monitor compliance and use of the shutter glasses by the user. Further, sensors can be included that monitor activity by the user which can be stored.

As previously described, an embodiment includes the application of shutter glasses therapy to the patient. For an embodiment, the therapy includes the patient wearing the shutter glasses approximately 1-2 hours a day, approximately 6-7 days a week, for at least approximately 6 weeks.

In another embodiment, through experimentation it has been determined that substantial results (improvement in patient condition) are realized by application of the shutter glasses therapy for approximately 6 weeks. Additional, but significantly less improvements can be realized for application of the shutter glasses therapy beyond the 6 weeks. For an embodiment, the use of the shutter glasses by the patient is monitored by a controller (such as, external controller 1700, or the internal controller 150, 1230, or a combination of both external controller 1700 and internal controller 150, 1230). Further, for an embodiment, the use is indicated to the patient or user. For an embodiment, the use is indicated to the user through a display (such as display 1060, display 1150, or a display of an external controller 1700). An embodiment includes providing an indicator to the patient when the user has satisfied a therapy use. For an embodiment, the therapy use comprises at least one of an hourly use, a daily use or a weekly use.

As previously described, for an embodiment, the shutter glasses include a shuttering or blanking rate of approximately 7 Hertz, plus or minus approximately 2 Hertz, having a duty cycle of approximately 50%.

For at least some embodiments, during therapy, the patient is able to perform near vision task, such as, reading, homework, computer viewing, and/or video games.

FIG. 18 is a flow chart that includes steps of a method of treating vision of a patient, according to an embodiment. A first step 1810 includes selecting a first period of blanking of a first lens of a corrective lens apparatus. A second step 1820 includes selecting a second period of blanking of a second lens of the corrective lens apparatus. For an embodiment, the first period and the second period are selected for treating a vision ailment of the patient. For example, the first period can be selected to be different than the second period to force one eye of the patient to work harder than the other eye of the patient. A third step 1830 includes selecting a frequency of at least one of the blanking of the first lens and the blanking of the second lens. For example, particular frequencies of blanking may be determined to be more effective in treating the patient than others. For an embodiment, the frequency is selective and adjustable depending upon how the shutter glasses are programmed or set.

One embodiment of the invention encourages the use of both eyes simultaneously so that the brain does not suppress input from one eye. Another embodiment helps an amblyopic eye to work harder. Other embodiments address other issues regarding the eyes.

As previously described, in a number of embodiments, the lenses of a pair of eyewear can be shuttered, and the shutter frequency can be adjusted. For example, the two lenses can be shuttered by alternately blanking the left and the right lens back and forth, with one lens shut and the other open, and vice versa. To illustrate, the shutter frequency can range from a few milliseconds to a few seconds. In one example, the shutter frequency can range from 1 Hz to 15 Hz. In another example, the shutter frequency can range from 6 to 10 Hz. In yet another example, the shutter frequency does not exceed the frequency where the shutter can be visually perceived by an average person. As to the increment within a range, the increment can be, for example, in 0.5 Hz, 1 Hz, 2 Hz, 3 Hz, or other increments.

In at least some embodiments, various ranges of shutter frequency for one or both of the two lenses are selectable. One embodiment includes a doctor or physician (or other) selecting the range or ranges of shutter frequency based at least in part on a vision or eye ailment of a patient or user. For example, a therapy of a first ailment may be optimally provided with a first range of shutter frequencies, and a therapy of a second ailment may be optimally provided with a second range of shutter frequencies. Other factors can influence the selected range of shutter frequency as well. For example, experimentation may determine that the desired shutter frequency changes with, for example, age, time, environment, race etc. One embodiment includes a doctor or physician (or other) selecting the shutter frequency based upon the results of one or more tests performed on the patient. For example, various ranges of shutter frequency may be tested by having the patient wear a pair of shutter glasses, and while wearing the shutter glasses operating at various shutter frequencies, having the patient perform one or more tests. As illustrations, one selected range can be from one to ten hertz. Another can extend the low end of the range to a period of one or more days.

One embodiment includes sensing when the patient is actually wearing a pair of shutter glasses. This can be done, for example, by incorporating a being-worn sensor in the glasses. The sensor can determine, for example, if the temples of the glasses are in the extended position. One embodiment further includes monitoring if the user is wearing the glasses. In one embodiment, a pair of shutter glasses includes a time sensor that times at least one of how long and how frequently the patient wears the glasses. For an embodiment, the time sensor is attached to, integral with, or being a part of the shutter glasses. For an embodiment, information related to the monitoring/sensing of the glasses is stored, such as in the glasses. For an embodiment, after stored, the monitoring information can be later retrieved, for example, by a doctor or physician to allow the physician to determine or gauge the compliance (e.g. duration of time of wearing the glasses) by the patient with the therapy suggested by the doctor of physician. The retrieval can be performed wired (e.g. via an electrical connector at the glasses) or wirelessly (e.g. via an infrared sensor at the glasses).

For one embodiment, a time sensor senses when the patient puts the shutter glasses on his/her head. As described, for an embodiment, this includes a "being worn" sensor. Another embodiment includes the time sensor being activated by a triggered event, such as, pressing a button or a switch located on the glasses.

In one embodiment, a motion detector is used as the "being worn" sensor. A threshold can be set, such that if the amount of motion exceeds the threshold, the eyewear is assumed to be worn. The motion detector can, for example, be achieved by a mechanical means or an accelerometer.

In another embodiment, the "being worn" sensor includes two thermal sensors. One sensor can be at approximately the middle of a temple, such as in a region that touches the head of the user wearing the glasses. The other sensor can be at the end of the temple, close to its hinge. If the temperature differential between the two sensors is beyond a certain preset value, the eyewear would be assumed to be worn. The differential is presumed to be caused by a person wearing the pair of glasses.

In yet another embodiment, the "being worn" sensor includes a stress sensor at the hinge of the temple. The assumption is that when the eyewear is worn, the hinge is typically slightly stretched because typically, the width of the head of the user is slightly wider than the width between the temples when the two temples are in the extended positions. If the value of the stress sensor is beyond a certain preset value, the glasses would be assumed to be worn.

In a further embodiment, the "being worn" sensor can be a switch. For example, at the hinge between a temple and its corresponding lens holder, there is a switch. When that temple is fully extended outwards, the switch is turned on. The switch can be a pin. When the temple is fully extended outwards, the pin is pressed. When both temples are fully extended outwards, in one embodiment, the glasses would be assumed to be worn by the user.

In addition to monitoring pertaining to the wearing of a pair of glasses by a patient, the monitoring can include monitoring the therapies applied to the patient. In yet another embodiment, the monitoring further includes monitoring characteristics of a patient. For example, eye movement or head movements of the patient while therapy is being applied through different types of sensors in the shutter glasses. Again, the monitoring information can be stored for later retrieval. For example, a doctor or physician can retrieve the monitoring information for not only a determination of compliance by the patient, but also to obtain additional patient information obtained while the patient is wearing the glasses and being treated with therapy provided by the shutter glasses.

In one embodiment with two lenses, the shuttering of each lens is controlled by a waveform, such as a voltage waveform, and the phase relationship between the waveforms of the two lenses can be adjusted. In one example, the phase can be approximately 90 degrees. In another example, the phase relationship can be at some other degrees.

In one embodiment, the shutter frequency of the two lenses can be independently controlled.

In one embodiment, the shutter lenses described herein can also modify its transmission or tint amount. As an example, the shutter lenses can auto-modulate to provide shading capability when used in sunny areas. As another example, the amount of transmission can be reduced manually, such as via a switch at the corresponding frame, if used before a bright monitor. It has been found that in some situations, the monitor brightness is directly related to computer-inflicted eye strain. In another embodiment, the two lenses of a frame can be independently adjustable for their transmission amount.

There can be different applications to changing the transmission coefficient. One example is for amblyopic eyes. The transmission coefficient of the lens for the good eye can be reduced to a very low level, such as 10% or less, or around 5%, instead of substantially blocking all the light to the good eye. Some users may feel more comfortable if their eyes could see something, instead of having all their vision blocked.

Another application regarding tinting or mirroring the lenses of a pair of shutter glasses is to make the shuttering less conspicuous. The low-frequency shuttering of the glasses may be visible to others who are proximate to the patient, thereby potentially drawing unwanted attention to the patient. This unwanted attention may cause the patient to not wear the glasses or wear the glasses less. By tinting or mirroring the lenses of the glasses, the effects of the shuttering may be at least partially disguised, thereby reducing the potential of unwanted attention by others. The tinting or mirroring of the lenses can be realized by, for example, coating the lenses with a mirror coat. In one embodiment, such coating can be known as a flash coating or a REVO coating.

In one embodiment, the transmission coefficient of a lens is not uniform across the lens. For example, the lens can be separated into zones. Using liquid crystal as an example, a lens driver circuit can provide electrical signals to one or more zones as in addressing liquid crystal display panels. To illustrate, the zones can be columns or vertical zones. As another illustration, the zones can be rows across a lens. In yet another illustration, a zone can be a region where a row intersects a column. With columns as an example, each column can be individually addressable by its corresponding conductors to control its transmission coefficient. One application of such an implementation is to train the brain to move an eye to areas of a lens where the eye could see. Assume that each of the two lenses of a pair of glasses is separated into ten evenly-spaced columns. After detailed analysis, an optometrist decides to block light, or at least a portion of the light, coming into the left side of the left eye so as to encourage the left eye to move more towards the nose. Then the optometrist operates the lens driver circuit so that the left three columns of the left lens block off light, with the remaining seven columns allowing light to go through. In another implementation, the lens driver circuit could implement a discrete gradient change in any direction using programmable transmission for each column.

In one embodiment, the transition for shuttering is not abrupt, but is gradual. In other words, the rate of change of the transmission coefficient can be gradually, such as in a linear or sinusoidal fashion, or via other types of waveforms. In some situations, a more gradual change in the transmission coefficient, such as during shuttering, can be more soothing to the eyes.

In one embodiment where the shuttering transition is more abrupt, such as in the waveform of a substantially rectangular wave, the on/off duty cycle of the shuttering of the lenses can be controlled. In one example, the duty cycle is 50%. In another example, the duty cycle is at some other percentages. In another embodiment with two lenses, the duty cycle of each of the lenses can be independently controlled.

In one example, an amblyopic eye can be forced to work harder by having its corresponding lens turned on longer than the other lens. In another example, there can be different blocking times for each lens, depending on which eye is more dominant or lazy. In yet another example, the lens for the normal eye can be shuttered, while the lens for the amblyopic eye is left unblocked, or does not shutter.

In one embodiment with two lenses, the change in transmission characteristics of each lens is controlled by a waveform, and the waveforms for the two lenses can be different. The two waveforms can differ in frequency, transmission amount, the abruptness of the shuttering if applicable, and/or the on/off duty cycle if applicable.

In one embodiment, the one or more attributes of the shutter lenses can be programmable via one or more switches on the corresponding frame. Examples of switches on a frame can include a knob, a slider or a small dial on the corresponding frame to program, such as the frequency of the shuttering or blanking. In another example, the one or more attributes of the shutter lenses can be programmed wirelessly, such as by a remote control.

In one embodiment, the shutter lenses can be integrated into prescription lenses, providing focal correction, such as bi-focal, tri-focal, prism, etc.

In one embodiment, the shutter lenses are based on liquid crystal lens technologies.

In one embodiment, an eyewear includes a single lens. As an example, the lens could be a single wrap-around lens.

In one embodiment, a distance between each lens of, for example, a pair of shutter glasses is no less than 13 mm, or the shortest distance between lenses is no less than 13 mm.

In one embodiment, the electronics for the shutter lenses are in an eyewear frame with the shutter lenses. In another embodiment, the shutter lenses with the corresponding electronics, such as the control circuitry, can be in a secondary frame, which is attachable to a primary frame via different mechanisms, such as magnets. The primary frame can include a pair of prescription lenses. To illustrate, there can be a housing or a chassis holding prescription lenses, with the shutter lenses provided on the outside, such as via a clip-on. In another example, the shutter lenses with the corresponding control circuitry can be in a fit-over frame that can fit over another frame.

In one embodiment, the electronic eyewear with shutter glasses is rechargeable or includes power sources, such as a battery, to allow the glasses to perform its operation over a duration of time, such as a few hours.

At least some embodiments include electronic-glasses therapy-providing systems and methods. For an embodiment, pre-selectable therapies are pre-stored, and accessible by a therapy provider (for example, a doctor or physician). For an embodiment, the pre-selectable therapies are based upon prior testing and experience with patients that suffer similar maladies. Based upon conditions being suffered by a present patient, one or more pre-selectable therapies can be downloaded to an electronic eyewear according to an embodiment. For an embodiment, a server, or a computer, accessible by a therapy provider, is operable to provide a user interface to the therapy provider that allows the therapy provider to easily select one of the pre-selectable therapies based on at least one condition of the patient (user). For an embodiment, the user interface includes a menu that provides therapy selections. The electronic therapy providing system provides an easy way for the therapy provider to select a therapy, and then down load to the electronic eyewear the selected therapy.

For an embodiment, a selected therapy is down loaded to an electronic eyewear of the patient from the therapy provider's computer, or from a remote server. As described, for an embodiment, the electronic eyewear includes a wired or wireless interface that allows the electronic eyewear to interface with an external controller, such as, the therapy provider's computer or the remote server.

At least some embodiments include monitoring the use of the electronic eyewear of the user (patient). The monitoring allows the patient and the therapy provider to have information regarding how well the patient has complied with the selected therapy. Further, with the monitoring of use, reminders can be provided to the user if the user is not properly complying with the suggested use of the electronic eyewear per the proscribed therapy. Further, the monitored use can be remotely communicated back to the therapy provider.

The monitored user further allows the therapy provider to determine how well the applied therapy is working. If the selected therapy is not working as desired, additional therapy selections can be made. The additional therapy selections can be aided by the monitored use of the electronic eyewear during the previously provided therapy. Again, for an embodiment, the additional selections can easily and/or automatically be made for or by the therapy provider. For an embodiment, the electronic-glasses therapy-providing systems and methods provide the additional selections, which, for an embodiment, can be made by the therapy provider through, for example, menus of a user interface.

For an embodiment, a therapy depends on the blanking frequency or a sequence of blanking frequencies. A downloaded therapy will automatically apply the corresponding blanking frequency to the shuttering eyewear of a user. For an embodiment, a physician observes the patient while the sequence of blanking frequencies is applied to the shuttering eyewear of the user. The physician can maintain the present setting; or based on monitoring or observation, the physician can adjust the blanking frequency or sequence of blanking frequencies being applied to the patient. This adjustment, for example, can be done via menu selection of different therapies by the physicians. In some situations, a patient's mind can fatigue to an applied blanking frequency, and the blanking frequency may no longer be effective. For an embodiment, the blanking frequency is changed to reduce or eliminate the effects of the fatigue. For at least some embodiments, the blanking frequency or sequence of blanking frequencies are predetermined and automatically selected and downloaded to the electronic eyewear of a user based on the conditions of the user.

Although specific embodiments have been described and illustrated, the embodiments are not to be limited to the specific forms or arrangements of parts so described and illustrated. The embodiments are limited only by the appended claims.

What is claimed:

1. A method of eye therapy, comprising:
   treating a user with shutter glasses therapy; wherein the shutter glasses therapy comprises:
   blanking a first lens of shutter glasses being worn by the user for a first blocking time;
   blanking a second lens of the shutter glasses being worn by the user for a second blocking time; and
   controllably setting at least one of the first blocking time and the second blocking time;
   wherein the shutter glasses include:
   a frame that includes a pair of arms forming eyewear that is adaptable to hold one or more lenses; and
   a pair of switches, wherein the pair of switches include a first switch and a second switch, wherein each switch of the pair of switches is located at a hinge formed between the frame and a corresponding one of the pair of arms, wherein each switch is open or closed depending upon an angle of the corresponding one of the pair of arms relative to a frontal plane of at least one of the one or more lenses;
   a display; and
   a controller, wherein the controller operates to:
   perform a first command when the first switch and the second switch are closed;
   perform a second command when the first switch is open and the second switch is closed;
   perform a third command when the first switch is closed and the second switch is open;
   perform a fourth command with when the first switch is open and the second switch is open;
   wherein a one of the first command, the second command, the third command, or the fourth command is selected to cause the controller to display on the display a first use parameter, and another one of the first command, the second command, the third command, or the fourth command is selected to cause the controller to display on the display a second use parameter.

2. The method of claim 1, further comprising not applying the shutter glasses therapy for a period of at least 1 month before treating the user with the shutter glasses therapy.

3. The method of claim 1, wherein the shutter glasses therapy includes having the first lens and the second lens alternate between blocking and non-blocking.

4. The method of claim 1, wherein the first blocking time is different than the second blocking time.

5. The method of claim 1, wherein the shutter glasses therapy includes a frequency in which at least one of the first lens and the second lens alternates between blocking and non-blocking is adjustable.

6. The method of claim 1, wherein the shutter glasses therapy includes a shuttering or blanking rate of approximately 7 Hertz, plus or minus approximately 2 Hertz, having a duty cycle of approximately 50%.

7. The method of claim 1, wherein an indicator indicates to the user when the user has satisfied a therapy use, wherein the therapy use comprises at least one of an hourly use, a daily use or a weekly use.

8. The method of claim 1, wherein monitoring a time of use of the shutter glasses by the user comprises monitoring how long at least one switch of the pair of switches is activated.

9. The method of claim 1,
   wherein the first use parameter indicates a daily use by the user, and the second user parameter indicates an accumulative use by the user.

10. The method of claim 9, wherein the use parameter includes when the eyewear has been worn by a user.

11. The method of claim 1, wherein at least a portion of the display is located on a bridge of the shutter glasses.

12. The method of claim 1, wherein at least a portion of the display is located on a lens of the shutter glasses.

13. The method of claim 1, wherein at least one switch includes a spring mechanism and a button, wherein the button is activated when the angle of the at least one of arms relative to the frontal plane of at least one of the one or more lenses exceeds a predetermined angle.

14. The method of claim 1, wherein another one of the first command, the second command, the third command, or the fourth command is selected to cause adjusting of a shuttering frequency of the first lens and the second lens.

15. An eye therapy system, comprising:
    shutter glasses, the shutter glasses comprising
    a frame that includes a pair of arms forming eyewear that is adaptable to hold one or more lenses; and
    a pair of switches, wherein the pair of switches include a first switch and a second switch, wherein each switch of the pair of switches is located at a hinge formed between the frame and a corresponding one of the pair of arms, wherein each switch is open or closed depending upon an angle of the corresponding one of the pair of arms relative to a frontal plane of at least one of the one or more lenses;
    a display; and
    a controller, the controller operative to treat a user with shutter glasses therapy; wherein during the shutter glasses therapy the controller is further operative to:
    blank a first lens of shutter glasses being worn by the user for a first blocking time;
    blank a second lens of the shutter glasses being worn by the user for a second blocking time;
    controllably set at least one of the first blocking time and the second blocking time;
    perform a first command when the first switch and the second switch are closed;
    perform a second command when the first switch is open and the second switch is closed;
    perform a third command when the first switch is closed and the second switch is open;
    perform a fourth command with when the first switch is open and the second switch is open;
    wherein a one of the first command, the second command, the third command, or the fourth command is selected to cause the controller to display on the display a first use parameter, and another one of the first command, the second command, the third command, or the fourth command is selected to cause the controller to display on the display a second use parameter.

16. The system of claim 15 wherein the controller is internal to the shutter glasses.

17. The system of claim 15, wherein the controller is external to the shutter glasses.

18. The system of claim 15, wherein the first use parameter indicates a daily use by the user, and the second user parameter indicates an accumulative use by the user.

19. The system of claim 15, wherein the controller is further operative to provide an indicator to the patient when the user has satisfied a therapy use.

20. The system of claim 19, wherein the therapy use comprises at least one of an hourly use, a daily use or a weekly use.

21. The system of claim 15, wherein another one of the first command, the second command, the third command, or the fourth command is selected to cause adjusting of a shuttering frequency of the first lens and the second lens.

* * * * *